United States Patent
Eldar-Finkelman

(10) Patent No.: US 7,157,422 B2
(45) Date of Patent: Jan. 2, 2007

(54) GLYCOGEN SYNTHASE KINASE-3 INHIBITORS

(75) Inventor: Hagit Eldar-Finkelman, Shoham (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 90 days.

(21) Appl. No.: 10/810,578

(22) Filed: Mar. 29, 2004

(65) Prior Publication Data

US 2004/0162234 A1   Aug. 19, 2004

Related U.S. Application Data

(60) Division of application No. 09/951,902, filed on Sep. 14, 2001, now Pat. No. 6,780,625, which is a continuation-in-part of application No. PCT/US01/00123, filed on Jan. 3, 2001.

(60) Provisional application No. 60/174,308, filed on Jan. 3, 2000, provisional application No. 60/206,115, filed on May 22, 2000.

(51) Int. Cl.
*A61K 38/03* (2006.01)
*C07K 4/00* (2006.01)

(52) U.S. Cl. ............... 514/7; 530/326; 530/327; 530/328; 530/329

(58) Field of Classification Search ............ None
See application file for complete search history.

(56) References Cited

U.S. PATENT DOCUMENTS

| | | | | |
|---|---|---|---|---|
| 6,057,117 A | | 5/2000 | Harrison et al. | ............ 435/7.93 |
| 6,153,618 A | | 11/2000 | Schultz et al. | ............ 514/261 |
| 6,441,140 B1 | * | 8/2002 | Comb et al. | ............ 530/387.1 |
| 6,495,376 B1 | * | 12/2002 | Lu et al. | ............ 436/501 |
| 6,780,625 B1 | * | 8/2004 | Eldar-Finkelman | ............ 435/194 |

FOREIGN PATENT DOCUMENTS

| | | |
|---|---|---|
| WO | WO 97/33601 A1 * | 9/1997 |
| WO | PCT WO 98/16528 | 4/1998 |
| WO | PCT WO 00/45237 | 3/2000 |
| WO | PCT WO 00/59206 | 5/2000 |
| WO | PCT WO 00/74663 | 12/2000 |
| WO | PCT WO 01/49709 | 7/2001 |
| WO | PCT WO 02/24941 | 3/2002 |

OTHER PUBLICATIONS

Jicha et al A Conformation- and Phosphorylation-Dependent Antibody Recognizing . . . Journal of Neurochemistry. 1997, vol. 69, No. 5, pp. 2087-2095.*

Eldar-Finkleman et al. "The Insulin Mimetic Action of Glycogen Synthase Kinase-3 Inhibitors", Diabetologia, 45(Suppl.2): A 70, 38th Annual Meeting for the European Association for the Study of Diabetes (EASD), Budapest, Hungary, 2002. Abstract.

Plotkin et al. "Insulin Mimetic Action of Synthetic Phosphorylated Peptide Inhibitors of Glycogen Synthase Kinase-3", Journal of Pharmacology and Experimental Therapeutics, 305(3): 974-980, 2003.

Leclerc et al. "Indirubins Inhibit Glycogen Synthase Kinase-3β and CDK5/P25, Two Proteins Kinases Involved in Abnormal Tau Phosphorylation in Alzheimer's Disease", The Journal of Biological Chemistry, 276(1): 251-260, 2001.

Hotamisligil et al. "IRS-1-Mediated Inhibition of Insulin Receptor Tyrosine Kinase Activity in TNT-α- and Obesity-Induced Insulin Resistance", Science, 271: 665-, 1996.

Tanti et al. "Serine/Threonine Phosphorylation of Insulin Receptor Substrate 1 Modulates Insulin Receptor Signaling", The Journal of Biological Chemistry, 269(8):6051-6057, 1994.

Fahraeus et al. "Inhibition of PRB Phosphorylation and Cell-Cycle Progression by a 20-Residue Peptide Derived from P16 CDKN2/INK4A", Current Biology, 6(1): 84-91, 1996.

Maniatis "Signal Transduction: Catalysis by a Multiprotein IkB Kinase Complex", Science, 278(5339): 818, 1997. Extract.

American Diabetes Association "Standards of Medical Care for Patients With Diabetes Mellitus", Diabetes Care, 17(6): 616-623, 1994.

Hawiger, J., "Non-Invasive Intracellular Delivery of Functional Peptides", Curr. Opin. Chem. Biol., 3:89-94, 1999.

* cited by examiner

*Primary Examiner*—Jeffrey Edwin Russel

(57) ABSTRACT

Peptide inhibitors of glycogen synthase kinase-3 (GSK-3) having an amino acid sequence motif of XZXXXS(p)X, wherein S(p)=phosphorylated serine or phosphorylated threonine, X=any amino acid, and Z=any amino acid except serine or threonine. These inhibitors, which are about 7 to 20 amino acids long, are specific for GSK-3 and strongly inhibit the enzyme with an $IC_{50}$ of about 150 μM. Also provided are methods of treating biological conditions mediated by GSK-3 activity, such as potentiating insulin signaling in a subject, treating or preventing type 2 diabetes in a patient, and treating Alzheimer's Disease by administering peptide inhibitors. Compositions of these peptide inhibitors and pharmaceutically acceptable carriers are also provided, as is a method for identifying inhibitors of GSK-3. The invention further relates to a computer-assisted method of structure based drug design of GSK-3 inhibitors using a three-dimensional structure of a peptide substrate of GSK-3.

6 Claims, 7 Drawing Sheets

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Ser residue 11 is phosphorylated.

<400> SEQUENCE: 1

Lys Arg Arg Glu Ile Leu Ser Arg Arg Pro Ser Tyr Arg
1               5                   10

<210> SEQ ID NO 2
<211> LENGTH: 13
<212> TYPE: PRT
<213> ORGANISM: Artificial Sequence
<220> FEATURE:
```

```
<223> OTHER INFORMATION: Synthetic

<400> SEQUENCE: 2

Lys Arg Arg Glu Ile Leu Ser Arg Arg Pro Ser Tyr Arg
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Ser residue 7 is phosphorylated.

<400> SEQUENCE: 3

Ile Leu Ser Arg Arg Pro Ser Tyr Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Ile Leu Ser Arg Arg Pro Glu Tyr Arg
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Ser residue 11 is phosphorylated.

<400> SEQUENCE: 5

Lys Arg Arg Glu Ile Leu Ala Arg Arg Pro Ser Tyr Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Ser residue 8 is phosphorylated.

<400> SEQUENCE: 6

Glu Ile Leu Ala Arg Arg Pro Ser Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (10)..(10)
<223> OTHER INFORMATION: Ser residue 10 is phosphorylated.

<400> SEQUENCE: 7

Lys Glu Glu Pro Pro Ala Pro Pro Gln Ser Pro
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Ser residue 10 is phosphorylated.

<400> SEQUENCE: 8

Lys Glu Ala Pro Pro Ala Pro Pro Gln Ser Pro
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Glu Pro Pro Ala Arg Arg Glu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Glu Pro Pro Ala Pro Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Ser residue 6 is phosphorylated.

<400> SEQUENCE: 11

Pro Ala Pro Pro Gln Ser Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic
```

-continued

```
<400> SEQUENCE: 12

Ile Leu Ser Arg Arg Pro Ser Tyr Arg
1               5
```

GLYCOGEN SYNTHASE KINASE-3 INHIBITORS

CROSS-REFERENCE TO RELATED APPLICATIONS

This is a divisional of U.S. patent application Ser. No. 09/951,902, filed Sep. 14, 2001 nos U.S. Pat. No. 6,780,625, which is a continuation-in-part of PCT/US01/00123 filed Jan. 3, 2001, which claims benefit of priority from U.S. Provisional application Nos. 60/174,308, filed Jan. 3, 2000, and 60/206,115, filed May 22, 2000. The entire contents of PCT/US01/00123, 60,174,308, and 60/206,115 are herein incorporated by reference.

BACKGROUND OF THE INVENTION

1. Field of the Invention

This invention relates generally to novel peptide inhibitors of glycogen synthase kinase-3 (GSK-3) and the use thereof for regulating biological conditions mediated by GSK-3 activity. The invention particularly relates to the use of such inhibitors to potentiate insulin signaling in type-2 diabetics, to treat neurodegenerative disorders as well as affective disorders, and to reduce neuronal cell death resulting from ischemic insult. The invention further relates to a computer-assisted method of structure based drug design of GSK-3 inhibitors based on the three-dimensional structure of a peptide substrate of GSK-3.

2. Description of the Related Art

Protein kinases, the enzymes that phosphorylate protein substrates, are key players in the signalling of extracellular events to the cytoplasm and the nucleus, and take part in practically any event relating to the life and death of cells, including mitosis, differentiation and apoptosis. As such, protein kinases have long been favorable drug targets. However, they have presented a problem in that the inhibition of many kinases could lead to cell death, because their activity is crucial to the well-being of the cell. Although this is a desirable effect for anticancer drugs, it is a major drawback for most other therapeutics. As a member of the family of protein kinases, glycogen synthase kinase-3 (GSK-3) is a cytoplasmic serine-threonine kinase that is involved in insulin signaling and metabolic regulation, as well as in Wnt signaling and the scheme of cell fate during embryonic development. Two similar isoforms of the enzyme, termed GSK-3α and GSK-3β, have been identified. The idea that GSK-3 is a favorable drug target among the protein kinase family is based on the fact that unlike other protein kinases, which are typically activated by signaling pathways, GSK-3 is normally activated in resting cells, and its activity is attenuated by the activation of certain signaling pathways such as after the binding of insulin to its cell-surface receptor. Activation of the insulin receptor leads to the activation of protein kinase B (PKB, also called Akt), which in turn phosphorylates GSK-3, thereby inactivating it. The inhibition of GSK-3 presumably leads to the activation of glycogen synthesis. The intricate insulin-signaling pathway is further complicated by negative-feedback regulation of insulin signaling by GSK-3 itself, which phosphorylates insulin-receptor substrate-1 on serine residues (Eldar-Finkelman et al., 1997).

Therefore, synthetic GSK-3 inhibitors might mimic the action of certain hormones and growth factors, such as insulin, which use the GSK-3 pathway. In certain pathological situations, this scheme might permit the bypassing of a defective receptor, or another faulty component of the signaling machinery, so that the biological signal will take effect even when some upstream players of the signaling cascade are at fault, such as in non-insulin-independent type 2 diabetes.

The regulation of glycogen catabolism in cells is a critical biological function that involves a complex array of signaling elements, including the hormone insulin. Through a variety of mediators, insulin exerts it regulatory effect by increasing the synthesis of glycogen by glycogen synthase (GS). A key event in insulin action is the phosphorylation of insulin receptor substrates (IRS-1, IRS-2) on multiple-tyrosine residues, which results in simultaneous activation of several signaling components, including PI3 kinase (Myers et al, 1992)). Similarly, the activity of glycogen synthase is suppressed by its phosphorylation.

One of the earliest changes associated with the onset of type 2 (non-insulin dependent) diabetes is insulin resistance. Insulin resistance is characterized by hyperinsulemia and hyperglycemia. Although the precise molecular mechanism underlying insulin resistance is unknown, defects in downstream components of the insulin signaling pathway may be the cause. Among the downstream components of insulin signaling is glycogen synthase kinase-3 (GSK-3), a serine/threonine kinase that has recently been recognized as an important signaling molecule in a variety of cellular processes. High activity of GSK-3 impairs insulin action in intact cells (Eldar-Finkelman et al, 1997). This impairment results from the phosphorylation of insulin receptor substrate-1 (IRS-1) serine residues by GSK-3. Likewise, increased GSK-3 activity expressed in cells results in suppression of glycogen synthase activity (Eldar-Finkelman et al, 1996). The laboratory of the present inventor found that GSK-3 activity is significantly increased in epididymal fat tissue of diabetic mice (Eldar-Finkelman et al, 1999). Subsequently, increased GSK-3 activity was detected in skeletal muscle of type 2 diabetes patients (Nickoulina et al, 2000). Thus, the inhibition of GSK-3 activity may represent a way to increase insulin activity in vivo.

GSK-3 is also considered to be an important player in the pathogenesis of Alzheimer's disease. GSK-3 was identified as one of the kinases that phosphorylates tau, a microtubule-associated protein, that is responsible for formation of paired helical filaments (PHF), an early characteristics of Alzheimer's disease. Apparently, abnormal hyperphosphorylation of tau is the cause for destabilization of microtubules and PHF formation. Despite the fact that several protein kinases were shown to promote phosphorylation of tau, only GSK-3 phosphorylation directly affected tau ability to promote microtubule self-assembly (Hanger et al., 1992; Mandelkow et al., 1992; Mulot et al., 1994; Mulot et al., 1995). Further evidence came from studies of cells overexpressing GSK-3 and from transgenic mice that specifically expressed GSK-3 in brain. In both cases GSK-3 led to generation of the PHF like epitope tau (Lucas et al., 2001).

Another mechanism that can link GSK-3 with Alzheimer's disease is its role in cell apoptosis. The fact that insulin is a survival factor of neurons (Barber et al., 2001) and initiates its anti-apoptotic action through activation of PI3 kinase and PKB (Barber et al., 2001), suggested that GSK-3, which is negatively regulated by these signaling components, promotes neuronal apoptosis. Studies have indeed confirmed this view, and showed that GSK-3 is critically important in life and death decision. Furthermore, its apoptotic function was shown to be independent of PI3 kinase. Overexpression of GSK-3 in PC12 cells caused apoptosis (Pap et al., 1998). Activation of GSK-3 in cerebellar granule neurons mediated migration and cell death (Tong et al., 2001). In human neuroblastoma SH-SY5Y cells, overexpression of GSK-3 facilitated stauroaporine-induced cell apoptosis (Bijur et al., 2000). Additional studies also indicated that inhibition of GSK-3 rescued cell death (as expected). These studies showed that expression of Fratl, a GSK-3 β inhibitor, was sufficient to rescue neurons from death induced by inhibition of PI3 kinase (Crowder et al., 2000). Recent work described the development of small molecules SB-216763 and SB-415286 (Glaxo SmithKline Pharmaceutical) that specifically inhibited GSK-3. Treatment of primary neurons with these compounds protected neuronal death induced by reduction in PI3 kinase activity (Cross et al., 2001).

Another implication of GSK-3 was detected in the context of affective disorders, i.e., bipolar disorder and manic depression. This linkage was based on the findings that lithium, a primary mood stabilizer frequently used in bipolar disease is a strong and specific inhibitor of GSK-3 at the therapeutic concentration range used in clinics (Klein et al., 1996; Stambolic et al., 1996; Phiel et al., 2001). The discovery has led to a series of studies that were undertaken to determine if lithium can mimic loss of GSK-3 activity in cellular processes. Indeed, lithium was shown to cause activation of glycogen synthesis (Cheng et al., 1983), stabilization and accumulation of β-catenin (Stambolic et al., 1996), induction of axis duplication in Xenopus embryo (Klein et al., 1996), and protection of neuronal death (Bijur et al., 2000). Altogether, these studies indicated that GSK-3 is a major in vivo target of lithium and thus has important implications in novel therapeutic treatment of affective disorders.

One mechanism by which lithium and other GSK3 inhibitors may act to treat bipolar disorder is to increase the survival of neurons subjected to aberrantly high levels of excitation induced by the neurotransmitter, glutamate (Nonaka et al., 1998). Glutamate-induced neuronal excitotoxicity is also believed to be major cause of neurodegeneration associated with acute damage, such as in cerebral ischemia, traumatic brain injury and bacterial infection. Furthermore, it is believed that excessive glutamate signaling is a factor in the chronic neuronal damage seen in diseases such as Alzheimer's, Huntington's, Parkinson's, AIDS associated dementia, amyotrophic lateral sclerosis (AML) and multiple sclerosis (MS) (Thomas, 1995). Consequently GSK3 inhibitors are believed to be a useful treatment in these and other neurodegenerative disorders.

While the inhibition of GSK-3 both by lithium chloride (LiCl) (PCT International patent application WO 97/41854) and by purine inhibitors (PCT International patent application WO 98/16528) has been reported, these inhibitors are not specific for GSK-3. Similarly, an engineered cAMP response element binding protein (CREB), a known substrate of GSK-3, has been described (Fiol et al, 1994), as have two peptide inhibitors of GSK-3 (Fiol et al, 1990). However, these substrates only nominally inhibit GSK-3 activity.

Recent work has demonstrated that GSK-3 is involved in additional cellular processes including development (He et al, 1995), oncogenesis (Rubinfeld et al, 1996) and protein synthesis (Welsh et al, 1993). Importantly, GSK-3 plays a negative role in these pathways. This suggests that GSK-3 is a cellular inhibitor in signaling pathways. Thus, development of specific drug inhibitors for GSK-3 will have important implications in basic research, as well as therapeutic interventions.

Thus, a need remains in the art for small, highly-specific, highly-effective peptide inhibitors of GSK-3. Such inhibitors would be useful in treating conditions associated with elevated GSK-3 activity such as diabetes type 2 (Eldar-Finkelman et al, 1997; Nikoulina et al, 2000), and with neurodegenerative disorders such as Alzheimer's disease (Mulot et al, 1995) and affective disorders such as manic depression (Manji et al, 1999).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The invention is directed to a highly effective and specific peptide inhibitors of glycogen synthase kinase-3 (GSK-3) and useful implications of these peptides. The peptide inhibitors of the invention include therewithin the amino acid motif XZXXXS(p)X, where S(p)=phosphorylated serine or phosphorylated threonine, X=any amino acid, and Z=any amino acid except serine or threonine. The peptides competitively bind to GSK-3 in vitro with high affinity. Because the amino acid Z in the motif is not phosphorylated, the peptide inhibitor cannot be phosphorylated. Thus, the peptide inhibits the catalytic activity of GSK-3, since the enzyme cannot proceed to phosphorylate other proteins.

The invention is based on the idea that short peptides derived from the recognition motif of GSK-3 may serve as inhibitors of the enzyme. The recognition motif of GSK-3 is SXXXS(p) where S=serine or threonine, X=any amino acid and S(p)=phosphorylated serine or phosphorylated threonine. This motif is unique to GSK-3. Because other protein kinases will not compete for this peptide, the GSK-3 inhibition motif is a specific and selective inhibitor for GSK-3.

The present invention presents a rationale and strategy to develop peptide inhibitors. The peptide inhibitors of the invention can be used to inhibit the activity of GSK-3 or to potentiate insulin signaling in vivo. The peptide inhibitors are useful for treating neurodegenerative disorders such as Alzheimer's disease, and affective disorders such as manic depression and bipolar disorder, for reducing neuronal cell death resulting from ischemic insult or from acute damage, such as traumatic brain injury, associated with glutamate-induced neuronal excitotoxicity, or for treating type 2 diabetes in a patient or preventing type 2 diabetes in a subject, as well as in identifying inhibitors of GSK-3. The peptide inhibitors are also useful therapeutic or research tools in the areas of oncogenesis, development, and metabolism, where GSK-3 has been shown to be important.

The present invention is also directed to a three-dimensional computer image of the three-dimensional structure of a peptide substrate of GSK-3, such as the peptide substrate p9CREB of SEQ ID NO:3.

Other aspects of the present invention relate to a computer-assisted method of structure based drug design of GSK-3 inhibitors using the three-dimensional structure of a peptide substrate of GSK-3 to design and to select a potential drug and also relate to a compound obtained according to this method that inhibits the phosphorylation activity of GSK-3.

The present invention further relates to a computer readable storage medium, which contains a set of three dimensional structural coordinate data of a peptide substrate of GSK-3 and to a computer for reproducing a three-dimensional representation of a peptide substrate of GSK-3.

DETAILED DESCRIPTION OF THE INVENTION

Figure 1:
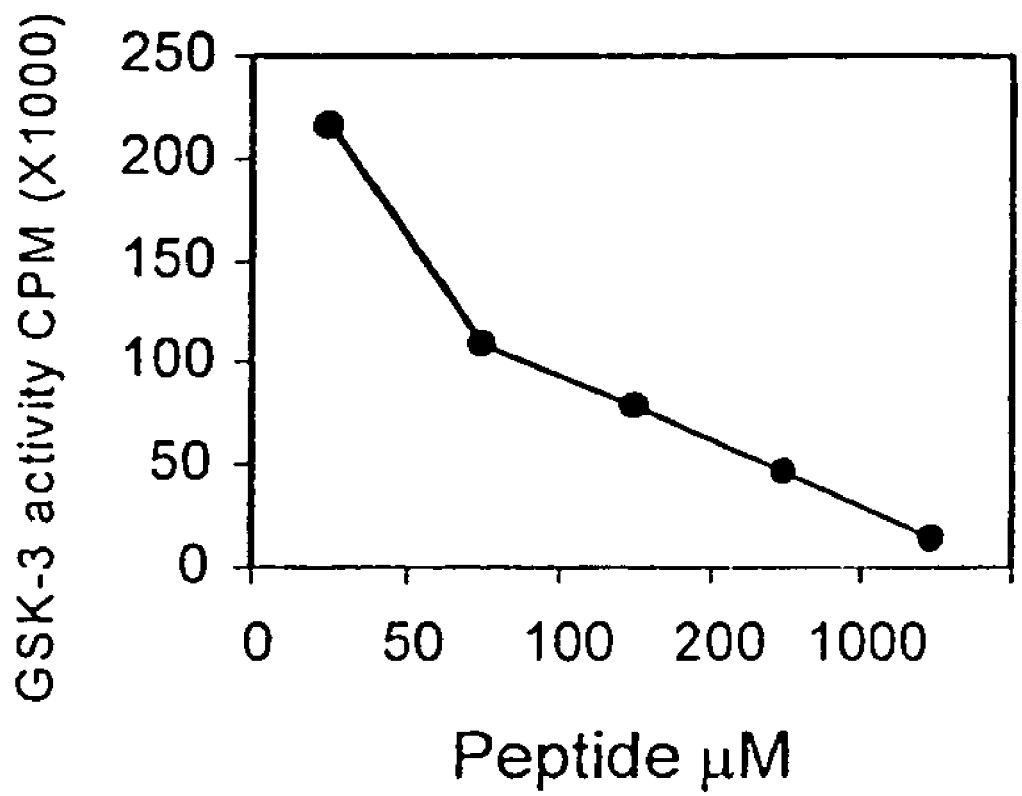
FIG. 1 is a graph showing inhibition of GSK-3 by peptide inhibitor. Purified GSK-3 enzyme was incubated with indicated concentrations of peptide #5 together with peptide substrate (PGS-1; Eldar-Finkelman et al., 1996) and $^{32}$P-labeled ATP. The reactions were incubated at 30° C. for 8 minutes. Reactions were spotted on p81 (phosphocellulose papers) washed with phosphoric acid and counted for radioactivity. Results are presented as $^{32}$P-incorporation into peptide.

The present invention is based on the concept that relatively short peptides, derived from the recognition motif of GSK-3, may serve as enzyme inhibitors. The recognition motif of GSK-3 is SXXXS(p), where S=serine or threonine, X=any amino acid, and S(p)=phosphorylated serine or phosphorylated threonine. This recognition motif is unique to GSK-3. In experiments designed to discover substrate inhibitors of GSK-3, it has been determined that the phosphorylated serine or threonine residue is necessary for binding. Without this residue, the peptide will neither be a substrate nor an inhibitor. In order to be a substrate, there must be a serine (or threonine) residue upstream of the phosphorylated serine (or threonine) residue separated by three additional residues. It has now been determined that replacing this upstream serine or threonine from the substrate recognition motif with a residue other than serine or threonine, the substrate peptide is converted from a substrate to an inhibitor. It is believed that at least one additional residue upstream and downstream of this motif is necessary in order to have an inhibitor of minimum size. Thus, the recognition motif which is believed to be necessary in order for the peptide to serve as an inhibitor is XZXXXS(p)X, where S(p)=phosphorylated serine or threonine, X is any amino acid, and Z is any amino acid except serine or threonine.

The preferred peptides in accordance with the present invention maintain the sequence of a known substrate except for the substitution of the serine or threonine that is at the fourth position upstream of the phosphorylated serine or threonine. When the known substrate from which the inhibitor is derived is the CREB protein, the minimum size of the inhibitor peptide is 10 residues, with the additional three residues all being upstream of the Z. Similarly, when the substrate from which the inhibitor is derived is heat shock factor-1 (HSF-1, the minimum number of residues in the inhibitor peptide must be greater than seven. It is known that a peptide of 11 residues is a strong inhibitor. Routine experimentation will determine whether peptides of 8, 9 and 10 residues inhibit or not. The present invention only comprehends the peptides within the formula of the present invention that are active as inhibitors.

Previously, Fiol et al (1990) experimented with glycogen synthase as a substrate of GSK-3 and determined that a peptide fragment, where the serine at the fourth position upstream of the phosphorylated serine in the recognition motif is substituted by alanine, has only very weak inhibiting activity. The present inventor has concluded that substrates which contain multiple recognition motifs behave differently from substrates which have only a single such recognition motif. Accordingly, the peptide inhibitors of the present invention will not comprehend peptides which contain multiple recognition motifs in the 20 residues upstream of the inhibition motif. Thus, the present invention specifically excludes peptides having two or more recognition motifs therein upstream of the inhibition motif. The preferred embodiment of the present invention are peptides having no recognition motifs. Indeed, the most preferred embodiments of the present invention are the shortest peptides having the inhibition motif of the present invention and which exhibit inhibition activity.

Thus, the present invention is directed to a novel class of peptide inhibitors of GSK-3, which exhibit high specificity for GSK-3 and strongly inhibit it with an IC$_{50}$ of about 150 µM, measured by in vitro kinase assay (see Example 2). The peptide inhibitors are "pseudosubstrates," because they have been derived and modified from the SXXXS(p) recognition motif of GSK-3. This strategy was exemplified by using two prototype peptides derived from CREB or HSF-1 proteins. One of the known substrates of GSK-3 is cAMP response element binding protein (CREB). The CREB sequence encompassing the GSK-3 recognition motif has been identified. CREB is phosphorylated at a single serine residue, $Ser_{133}$, to create the sequence motif SXXXS(p), where S(p) denotes phosphorylated serine, which serves as the minimal GSK-3 recognition sequence (Fiol et al, 1987; Fiol et al, 1988).

The peptides are small, synthetic peptides of about 7 to 50 amino acids and have as part of their sequence the amino acid motif XZXXXS(p)X, where S(p)=phosphorylated serine or threonine, X=any amino acid, and Z=any amino acid except serine or threonine. Because the amino acid Z in the motif is not phosphorylated, the peptide inhibitor cannot be phosphorylated. Thus, the peptide inhibits the catalytic activity of GSK-3 because the enzyme cannot proceed to phosphorylate other proteins.

Peptide inhibitors of the present invention inhibit both GSK-3 substrate phosphorylation and autophosphorylation on a level comparable to LiCl (see EXAMPLE 2), as measured by in vitro kinase assay.

Peptide inhibitors of about 7–10 amino acid residues or greater are sufficient to inhibit GSK-3 activity. The peptide inhibitors can be about 10–13 amino acid residues in length. Also, the peptide inhibitors can be about 7–50 amino acids in length. Inhibitors of 7–20 amino acid residues in length are preferred, with a length of 10–20 amino acids being more preferred, and 10–13 amino acids most preferred.

Most of the GSK-3 substrates which do not contain multiple recognition motifs have a glutamic acid residue three residues upstream of the first serine residue of the recognition motif. When this glutamic acid is replaced by another amino acid residue, the inhibiting activity of the peptides of the present invention are further improved. Accordingly, a further preferred embodiment of the present invention are peptides in which the residue three residues upstream of Z is other than glutamic acid.

The inhibition of GSK-3 activity is a way to increase insulin activity in vivo. High activity of GSK-3 impairs insulin action in intact cells (Eldar-Finkelman et al, 1997). This impairment results from the phosphorylation of insulin receptor substrate-1 (IRS-1) serine residues by GSK-3. Studies performed in patients with type 2 diabetes (non-insulin dependent diabetes mellitus, NIDDM) show that glycogen synthase activity is markedly decreased these patients, and that decreased activation of protein kinase B (PKB), an upstream regulator of GSK-3, by insulin is also detected (Shulman et al, (1990); Nikoulina et al, (1997); Cross et al, (1995). Mice susceptible to high fat diet-induced diabetes and obesity have significantly increased GSK-3 activity in epididymal fat tissue (Eldar-Finkelman et al, 1999). Increased GSK-3 activity is expressed in cells resulted in suppression of glycogen synthase activity (Eldar-Finkelman et al, 1996). Thus, inhibition of GSK-3 activity provides a useful method for increasing insulin activity in insulin-dependent conditions.

An inhibitor that "potentiates insulin signaling" is an inhibitor which, when administered, increases the phosphorylation of insulin receptor downstream components and increases the rate of glucose uptake as compared to glucose uptake in a subject not administered the inhibitor.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of type 2 diabetes means alleviating, ameliorating, inhibiting, reducing, or curing the clinical manifestations of type 2 diabetes, either transiently or permanently, including slowing the rate of glucose uptake. Such treatment includes the potentiation of insulin signaling. The "preventing" of type 2 diabetes means inhibiting, delaying, slowing, or preventing the onset of clinical manifestations of type 2 diabetes, either transiently or permanently, including slow rate of glucose uptake. Such prevention includes potentiation of insulin signaling. An "amount effective to potentiate insulin signaling" is the dose of inhibitor needed to effectively potentiate insulin signaling in a subject. Treatment of a neurodegenerative disorder such as Alzheimer's disease may halt or retard the progression of the disease (e.g., as measured by a reduction in the rate of dementia). Treatment of an affective disorder such as mamic depression or bipolar disorder may alleviate or stop the symptoms of the disorders. Treatment of conditions of ischemic insult, as cerebral stroke may prevent, halt or reduce neuronal cell death.

The term "biological condition mediated by GSK3 activity" as used herein refers to any biological or medical condition or disorder in which effective GSK3 activity is identified, whether at normal or abnormal levels. The condition or disorder may be caused by the GSK3 activity or may simply be characterized by GSK3 activity. That the condition is mediated by GSK3 activity means that some aspect of the condition can be traced to the GSK3 activity. It is expected that by the method of the invention, inhibiting the GSK3 activity will then prevent, ameliorate or treat the condition so characterized.

Method of Making Peptide Inhibitors

The amino acid residues described herein are preferably in the "L" isomeric form. However, residues in the "D" isomeric form can be substituted for any L-amino acid residue, as long as the peptide inhibitors retain specificity for GSK-3. This definition includes, unless otherwise specifically indicated, chemically-modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

In other words, the peptide can be a peptide "mimetic". Thus, one aspect of the present invention provides for peptidomimetics which mimic the structural features of the critical amino acid motif XZXXXS(p)X.

Although most inhibitors of GSK-3 are expected to be peptides, by the use of the screening method and the computer-assisted method of structure based drug design described below, other non-peptide inhibitors of GSK-3 can be identified. The peptidomimetics that are non-peptide in nature can be designed and synthesized by standard organic chemical methods. The peptidomimetics that are non-peptide in nature can be even more advantageous in therapeutic use, in the resistance to degradation, in permeability and in possible oral administration.

Peptidomimetics are small molecules that can bind to proteins by mimicking certain structural aspects of peptides and proteins. They are used extensively in science and medicine as agonists and antagonists of protein and peptide ligands of cellular and other receptors, and as substrates and substrate analogs for enzymes. Some examples are morphine alkaloids (naturally-occurring endorphin analogs), penicillins (semi-synthetic), and HIV protease inhibitors (synthetic). Such compounds have structural features that mimic a peptide or a protein and as such are recognized and bound by other proteins. Binding the peptidomimetic either induces the binding protein to carry out the normal function caused by such binding (agonist) or disrupts such function (antagonist, inhibitor).

A primary goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogs have been obtained. In some instances, these analogs have been shown to possess longer biological half-lives than their naturally-occurring counterparts In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of γ-lactam or other types of bridges. See, e.g., Veber et al, (1978) and Thorsett et al (1983).

Another approach, disclosed by Rich (1986), has been to design peptide mimics through the application of the transition state analog concept in enzyme inhibitor design. For example, it is known that the secondary alcohol of statine mimics the tetrahedral transition state of the sessile amide bond of the pepsin substrate Nicolaou et al (1990) disclosed non-peptide somatostatin mimics.

In U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups which cause the compounds to be at least partially crossreactive with the peptide. As will be recognized, compounds which mimic or inhibit peptides are to varying degrees crossreactive therewith. Other techniques for preparing peptidomimetics are disclosed in U.S. Pat. Nos. 5,550,251 and 5,288,707, for example.

Protein phosphorylation plays a crucial part in the biochemical control of cellular activity. Phosphorylation usually means formation of a phosphate ester bond between a phosphate ($PO_4$) group and an amino acid containing a hydroxyl (OH) group (tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off.

Phosphopeptide mimetics are a subclass of peptidomimetics that contain analogs of phosphorylated tyrosine, serine and threonine. Phosphate esters may be hydrolyzed by various enzymes, thus turning off a phosphorylation signal. Phosphopeptide mimetics, however, usually contain non-hydrolyzable analogs to prevent inactivation (Burke et al, 1994a; Burke et al, 1996a; Chen et al, 1995; Wiemann et al, 2000; Shapiro et al, 1997; Otaka et al, 1995; Otaka et al, 2000). General examples of phosphopeptide mimetics in the art include SH2 domain analogs (Burke et al, 1994a; Fu et al, 1998; Gao et al, 2000; Mikol et al, 1995; Ye et al, 1995), transcription factor NF-(kappa)B analog (McKinsey et al, 1997), P53 analog (Higashimoto et al, 2000) and protein-tyrosine phosphatase inhibitors (Burke et al, 1994b; Burke et al, 1996b; Groves et al, 1998; Kole et al, 1995; Kole et al, 1997; Roller et al, 1998).

Commercially available software packages can be used to design small peptides and/or peptidomimetics containing, phosphoserine or phosphothreonine analogs, preferably non-hydrolyzable analogs, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

The peptide inhibitors of the present invention also include salts and chemical derivatives of the peptides. "Chemical derivative" refers to a polypeptide of the invention having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

Some useful modifications are designed to increase the stability of the peptide inhibitor in solution and, therefore, serve to prolong the half-life of the peptide inhibitor in solutions, particularly biological fluids, such as blood, plasma or serum, by blocking proteolytic activity in the blood. A peptide inhibitor can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the peptide inhibitor, and amide rather than amino or carboxy termini to inhibit exopeptidase activity.

A peptide inhibitor of the invention may or may not be glycosylated. The peptide inhibitors are not glycosylated, for example, when produced directly by peptide synthesis techniques or are produced in a prokaryotic cell transformed with a recombinant polynucleotide. Eukaryotically-produced peptide molecules are typically glycosylated.

The peptide inhibitors of the invention can be produced by well known chemical procedures, such as solution or solid-phase peptide synthesis, or semi-synthesis in solution beginning with protein fragments coupled through conventional solution methods, as described by Dugas et al (1981). Alternatively, a peptide inhibitor of the invention can be synthesized by using well known methods, including recombinant methods and chemical synthesis.

A peptide inhibitor of the invention can be chemically synthesized, for example, by the solid phase peptide synthesis of Merrifield et al (1964). Alternatively, a peptide inhibitor of the invention can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

The peptide inhibitors of the invention are particularly useful when they are maintained in a constrained secondary conformation. The terms "constrained secondary structure," "stabilized" and "conformationally stabilized" indicate that the peptide bonds comprising the peptide are not able to rotate freely but instead are maintained in a relatively fixed structure. A method for constraining the secondary structure of a newly synthesized linear peptide is to cyclize the peptide using any of various methods well known in the art. For example, a cyclized peptide inhibitor of the invention can be prepared by forming a peptide bond between non-adjacent amino acid residues as described, for example, by Schiller et al (1985). Peptides can be synthesized on the Merrifield resin by assembling the linear peptide chain using $N^\alpha$-Fmoc-amino acids and Boc and tertiary-butyl proteins. Following the release of the peptide from the resin, a peptide bond can be formed between the amino and carboxy termini.

A newly synthesized linear peptide can also be cyclized by the formation of a bond between reactive amino acid side chains. For example, a peptide containing a cysteine-pair can be synthesized, with a disulfide bridge, can be formed by oxidizing a dilute aqueous solution of the peptide with $K_3Fe(CN)_6$. Alternatively, a lactam such as an $\epsilon$-($\gamma$-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, 1997). Methods for forming these and other bonds are well known in the art and are based on well-known rules of chemical reactivity (Morrison et al, 1992).

Alternatively, the peptide inhibitor of the invention can be produced recombinantly. Systems for cloning and expressing polypeptide of the invention include various microorganisms and cells that are well known in recombinant technology. These include, for example, various strains of *E. coli, Bacillus, Streptomyces*, and *Saccharomyces*, as well as mammalian, yeast and insect cells. The peptide inhibitor of the invention can be produced as a peptide or fusion protein. Suitable vectors for producing the peptide inhibitor are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Pharmaceutical Compositions

The invention provides pharmaceutical compositions comprising a therapeutically effective dose of the peptide inhibitor of the invention in a pharmaceutically acceptable excipient, for administration to a subject, such as a human patient.

Therapeutically effective amount" as used herein refers to that amount that is effective to obtain the desired therapeutic result. The term "an effective amount" of an inhibitor of GSK3 refers to an amount that is effective to induce an inhibition of GSK3 activity. That activity can be GSK3 kinase activity. The inhibitory amount may be determined directly by measuring the inhibition of a GSK3 activity, or, for example, where the desired effect is an effect on an activity downstream of GSK3 activity in a pathway that includes GSK3, the inhibition may be measured by measuring a downstream effect. Thus, for example where inhibition of GSK3 results in the arrest of phosphorylation of glycogen synthase, the effects of the inhibitor may be effects on an insulin-dependent or insulin-related pathway, and the inhibitor may be administered to the point where glucose uptake is increased to optimal levels. Also, where the inhibition of GSK3 results in the absence of phosphorylation of a protein that is required for further biological activity, for example, the tau protein, then the inhibitor may be administered until polymerization of phosphorylated tau protein is substantially arrested. Therefore, the inhibition of GSK3 activity will depend in part on the nature of the inhibited pathway or process that involves GSK3 activity, and on the effects that inhibition of GSK3 activity has in a given biological context.

The amount of the inhibitor that will constitute an inhibitory amount will vary depending on such parameters as the inhibitor and its potency, the half-life of the inhibitor in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the inhibitor or that will have an effect on GSK3 activity, or a pathway mediated by GSK3 activity. It is expected that the inhibitory amount will fall in a relatively broad range that can be determined through routine trials.

"Co-administration" as used herein means administration of an inhibitor of GSK3 according to the method of the invention in combination with a second therapeutic agent. The second therapeutic agent can be any therapeutic agent useful for treatment of the patient's condition. For example, inhibition of GSK3 with lithium as a second therapeutic agent used in conjunction with a therapeutic agent inhibitor of GSK3 is contemplated. Additionally, for example, a first therapeutic agent can be a small molecule inhibitor of GSK3 activity, and a second therapeutic agent can be an antisense or ribozyme molecule against GSK3 that, when administered in a viral or nonviral vector, will facilitate a transcriptional inhibition of GSK3 that will complement the inhibitory activity of the small molecule. The second therapeutic agent can also be lithium ion. Co-administration may be simultaneous, for example, by administering a mixture of the therapeutic agents, or may be accomplished by administration of the agents separately, such as within a short time period. Co-administration also includes successive administration of an inhibitor of GSK3 and one or more of another therapeutic agent. The second therapeutic agent or agents may be administered before or after the inhibitor of GSK3. The second therapeutic agent may also be an inhibitor of GSK3, which has particular advantages when administered with the first inhibitor. Dosage treatment may be a single dose schedule or a multiple dose schedule.

The term "pharmaceutically acceptable excipient" includes any solvents, dispersion media, antibacterial and antifungal agents, microcapsules, liposomes, cationic lipid carriers, isotonic and absorption delaying agents and the like which are not incompatible with the active ingredients. The formulation of pharmaceutical compositions is generally known in the art; reference can conveniently be made to *Remington's Pharmaceutical Sciences*, 18th Ed. (Mack Publishing Co., Easton, Pa.). Thus, the pharmaceutical compositions can comprise a suitable application medium, such as a gel, salve, lotion, colloid or powder, aqueous solutions such as physiologically buffered saline or other solvents or vehicles such as glycols, glycerol, oils such as olive oil or injectable organic esters. Pharmaceutical compositions can be prepared as injectables, either as liquid solutions or suspensions. The preparation can also be emulsified. The skilled artisan will recognize that any pharmaceutically acceptable means for effecting the introduction of peptide inhibitors into target cells is suitable.

Physiologically acceptable excipients include, for example, carbohydrates, such as glucose, sucrose or dextrans, antioxidants, such as ascorbic acid or glutathione, chelating agents, low molecular weight proteins or other stabilizers or excipients. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents that enhance the effectiveness of the active ingredient. A peptide inhibitor can also be formulated into the pharmaceutical composition as neutralized pharmaceutically acceptable salt forms. Pharmaceutically acceptable salts include the acid addition salts (formed with the free amino groups of the peptide inhibitor or antibody molecule) that are formed with inorganic acids such as, for example, hydrochloric or phosphoric acids, or such organic acids as acetic, tartaric, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical forms suitable for infusion include sterile aqueous solutions or dispersions and sterile powders for the extemporaneous preparation of sterile injectable solutions or dispersion. The form is fluid to the extent that easy syringability exists. Typical excipients include a solvent or dispersion medium containing, for example, water-buffered aqueous solutions (i.e., biocompatible buffers), ethanol, polyols, such as glycerol, propylene glycol, polyethylene glycol, suitable mixtures thereof, surfactants, or vegetable oils. Sterilization can be accomplished by any art-recognized technique including, but not limited to, filtration or addition of antibacterial or antifungal agents, for example, paraben, chlorobutanol, phenol, sorbic acid or thimerosal. Further, isotonic agents, such as sugars or sodium chloride, may be incorporated in the pharmaceutical compositions. Prevention against microorganism contamination can be achieved through the addition of various antibacterial and antifungal agents.

Methods of Administration

The peptide inhibitors of the invention can be administered to a subject in any manner known to those of skill in the art which is suitable for the introduction of peptide inhibitor into target cells. For example, the administration of peptide inhibitor blocks about 50% or greater of GSK-3 phosphorylation activity, as measured by in vitro kinase assay (see Example 2).

The peptide inhibitors of the invention can be administered in any way that is medically acceptable. The mode of administration can depend on the disease condition or injury being treated. Possible administration routes include injections, by parenteral routes, such as intravascular, intravenous, intra-arterial, subcutaneous, intramuscular, intratumor, intraperitoneal, intraventricular, intraepidural or others, as well as oral, nasal, ophthalmic, rectal, topical, or by inhalation. Sustained release administration is also specifically included in the invention, by such means as depot injections or erodible implants. Administration can also be intra-articularly, intrarectally, intraperitoneally, intramuscularly, subcutaneously, or by aerosol inhalant. Where treatment is systemic due, the composition can be administered orally or parenterally, such as intravenously, intramuscularly, subcutaneously, intraorbitally, intracapsularly, intraperitoneally or intracisternally, as long as provided in a composition suitable for effecting the introduction of the peptide inhibitor into target cells.

The pharmaceutical compositions can be administered intravenously, as by injection of a unit dose. The term "unit dose" when used in reference to a pharmaceutical composition of the invention refers to physically discrete units suitable as unitary dosages for humans, each unit containing a predetermined quantity of active material calculated to produce the desired therapeutic effect.

The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges can be one to several mg of active ingredient per individual per day and depend on the route of administration. Suitable regimes for initial administration and booster shots are typified by an initial administration followed by repeated doses at one or more hour intervals by a subsequent injection or other administration. Alternatively, continuous intravenous infusion sufficient to maintain therapeutically effective concentrations in the blood are contemplated. Whenever, the peptide inhibitors of the invention are used for promoting attachment of cells, such compositions will typically have a higher concentration than those taken internally.

Dosage

The precise therapeutically-effective amount of peptide inhibitor of the invention used in the methods of this invention applied to humans can be determined by the ordinarily-skilled artisan with consideration of individual differences in age, weight, extent of cellular infiltration by inflammatory cells and condition of the patient. The pharmaceutical preparation of the invention should be administered to provide an effective concentration of 5–100 µM, preferably about 5 µM.

The concentration of a peptide inhibitor of the invention required to obtain an effective dose in a subject depends on many factors including the age and general health of the subject as well as the route of administration and the number of treatments to be administered. The total effective amount of a peptide inhibitor of the invention can be administered to a subject as a single dose, either as a bolus or by infusion over a relatively short period of time, or can be administered using a fractionated treatment protocol, in which the multiple doses are administered over a more prolonged period of time.

It is especially advantageous to formulate parenteral compositions in dosage unit form for ease of administration and uniformity of dosage. "Dosage unit form" refers to physically discrete units suited as unitary dosages for the mammalian subjects to be treated, each unit containing a predetermined quantity of active material calculated to produce the desired therapeutic effect in association with the required pharmaceutical excipient. A pharmaceutical composition typically contains an amount of at least 0.1 weight % of active ingredient, i.e., a peptide inhibitor or antibody of this invention, per weight of total pharmaceutical composition. A weight % is a ratio by weight of active ingredient to total composition. Thus, for example, 0.1 weight % is 0.1 grams of peptide inhibitor per 100 grams of total composition.

Methods for Inhibiting the Activity of GSK-3

The peptide inhibitors of the invention are used to inhibit the activity of GSK-3 in a cell. Cells are contacted with a peptide inhibitor in an amount effective to inhibit GSK-activity in vitro. The peptide inhibitors of the invention can be used to potentiate insulin signaling in a subject, in vivo. The inhibitor is administered to the subject in an amount effective to increase basal GS activity in intact cells (see Example 3).

Methods for Treating a Biological Condition Mediated by GSK-3 Activity

As a further aspect of the present invention, the peptide inhibitors of the invention can be used to treat a biological condition mediated by GSK-3 activity. The biological condition mediated by GSK-3 activity includes non-insulin dependent diabetes mellitus as is described below. The biological condition further includes neurodegenerative disorders such as Alzheimer's disease, affective disorders such as bipolar disorder and manic depression, and neuronal cell death resulting from ischemic insult such as from a cerebral stroke.

Methods for Potentiating Insulin Signaling

Potentiation of insulin signaling, in vivo, resulting from administration of the GSK-3 peptide inhibitors of the invention can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of peptide inhibitor to an insulin-resistant patient increases the rate of glucose uptake as compared to a non-treated patient. Peptide inhibitor may be administered to an insulin resistant patient for a longer period of time, and the levels of insulin, glucose, and leptin in blood circulation (which are usually high) may be determined. Decrease in glucose levels will indicate that the peptide inhibitor potentiated insulin action. A decrease in insulin and leptin levels alone may not necessarily indicate potentiation of insulin action, but rather will indicate improvement of the disease condition by other mechanisms.

Methods for Treating Diabetes

Diabetes mellitus is a heterogeneous primary disorder of carbohydrate metabolism with multiple etiologic factors that generally involve insulin deficiency or insulin resistance or both. Type I, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type II diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The peptide inhibitors of the invention can be used to therapeutically treat type 2 diabetes in a patient with type 2 diabetes. A therapeutically effective amount of the inhibitor is administered to the patient, and clinical markers, or example blood sugar level, are monitored. The peptide inhibitors of the invention can further be used to prevent type 2 diabetes in a subject. A prophylactically effective amount of the inhibitor is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80–120 milligrams per deciliter (mg/dl) before meals and 100–140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level ($HbA_{1c}$; a measure of average blood glucose levels over the past 2–3 months, normal range being 4–6%), tests for cholesterol and fat levels, and tests. for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Methods for Identifying Inhibitors of Insulin Signaling

The peptide inhibitors of the invention are used to identify inhibitors of GSK-3. Inhibitors of GSK-3 can be identified in a screening assay, using a peptide inhibitor of the invention as a positive control.

In one screening method, a first cell is contacted with a test compound that is suspected of interfering with insulin signaling. A second cell with a peptide inhibitor of the invention is contacted with the same test compound. The insulin signal for the first cell is then compared with the insulin signaling for an uncontacted cell and with the insulin signaling for the second cell. A decrease in insulin signaling for the first cell, as compared with the insulin signaling for an uncontacted cell and with the insulin signaling for the second cell, identifies the compound as a compound that interferes with GSK-3 signaling.

Computer Representation

The 2D $^1$H NMR spectra coordinate data of a peptide substrate of GSK-3, such as cAMP response element binding protein (CREB), heat shock factor-1 (HSF-1), Inhibitor 2, G subunit, ATP-citrate lyase, elongation factor eIF2B, or fragments thereof, when used in conjunction with a computer programmed with software to translate those spectra into the 3-dimensional structure of a peptide substrate of GSK-3, may be used for a variety of purposes, especially for purposes relating to drug discovery. Such software for generating 3-dimensional graphical representations from spectral coordinate data are known and commercially available, i.e., RASMOLE, and the software INSIGHTII, CERIUS2 and CATALYST produced by Accelyrs. The ready use of the spectra data requires that it be stored in a computer-readable format. Thus, in accordance with the present invention, data capable of being displayed as the 3-dimensional structure of a peptide substrate of GSK-3 and portions thereof and their structurally similar homologs is stored in a machine-readable storage medium, which is capable of displaying a graphical 3-dimenslonal representation of the structure.

Therefore, another embodiment of this invention provides a machine-readable data storage medium, comprising a data storage material encoded with machine-readable data which, when used by a machine programmed with instructions for using said data, displays a graphical 3-dimensional representation of a peptide substrate of GSK-3.

Even more preferred is a machine-readable data storage medium that is capable of displaying a graphical 3-dimensional representation of a CREB peptide substrate of GSK-3 comprising the amino acid sequence of SEQ ID NO:3 and defined by the structure coordinate data of all of the atoms in Table 3.

According to an alternate embodiment, this invention provides a computer for producing a 3-dimensional representation of a peptide substrate of GSK-3, wherein said computer comprises:

(a) a machine-readable data storage medium comprising a data storage material encoded with machine-readable data, wherein said machine-readable data comprises the spectra data or structure coordinate data of the peptide substrate of GSK-3 or portions/fragments thereof;

(b) a working memory for storing instructions for processing said machine-readable data;

(c) a central-processing unit coupled to said working memory and to said machine-readable data storage medium, for processing said machine-readable data into said 3-dimensional representation; and (d) an output hardware coupled to said central processing unit, for receiving said 3-dimensional representation.

Figure 7:
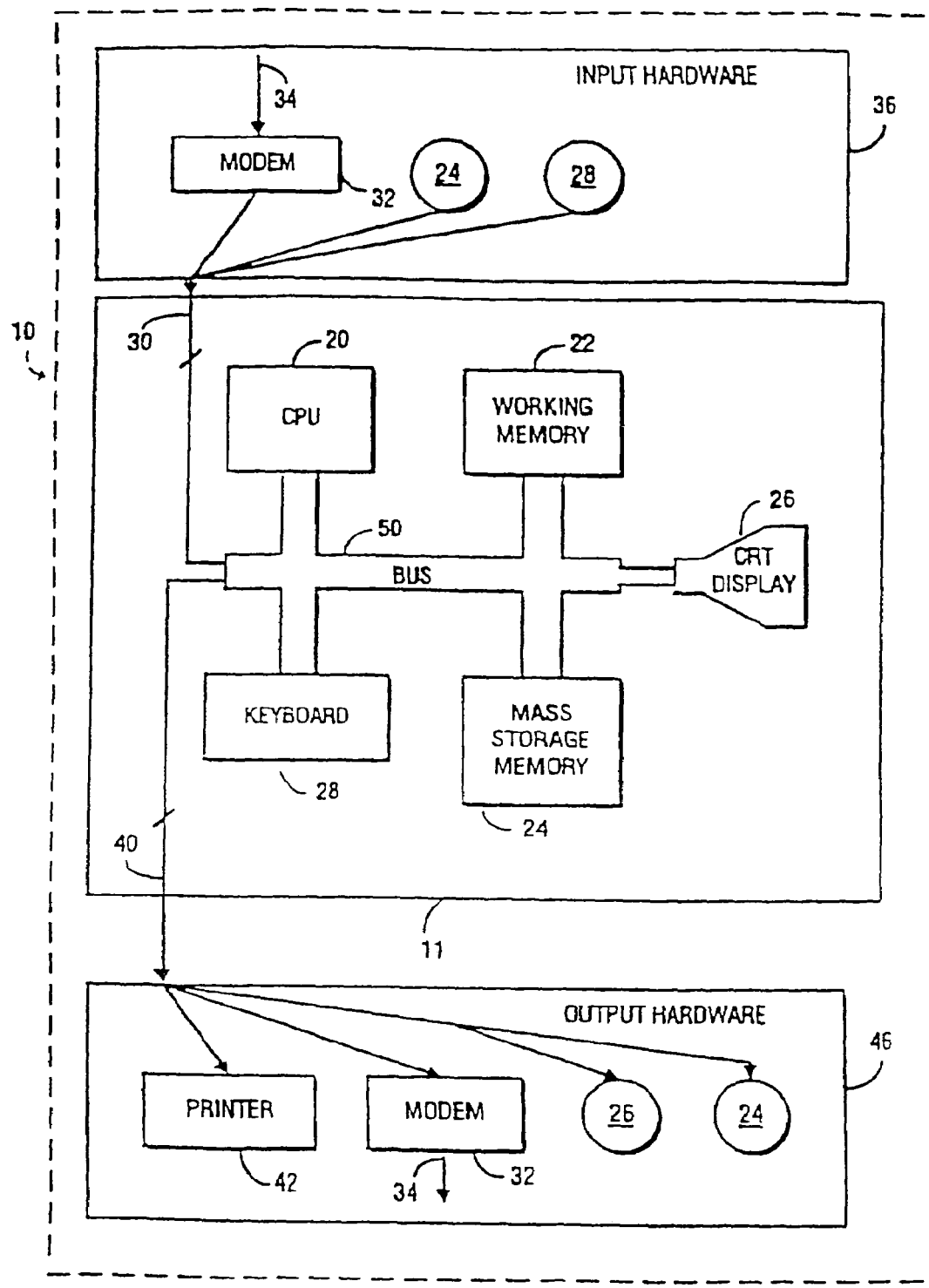
FIG. 7 shows a diagram of a system used to carry out the storage medium of FIGS. 8 and 9.

FIG. 7 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of the 3D structure of a peptide substrate of GSK-3 using a-program such as INSIGHTII as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

Figure 8:
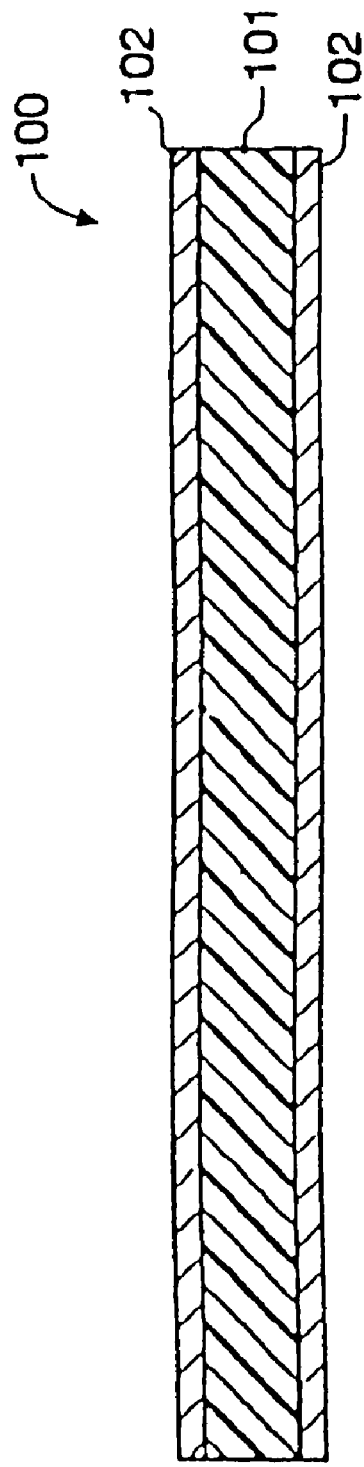
FIG. 8 shows a cross-section of a magnetic storage medium.

FIG. 8 shows a cross section of a magnetic data storage medium 100 which can be encoded with a machine-readable data that can be carried out by a system such as system 10 of FIG. 7. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24. The magnetic domains of coating 102 of medium 100 are polarized or oriented so as to encode in manner which may be conventional, machine-readable data such as that described herein, for execution by a system such as system 10 of FIG. 7.

Figure 9:
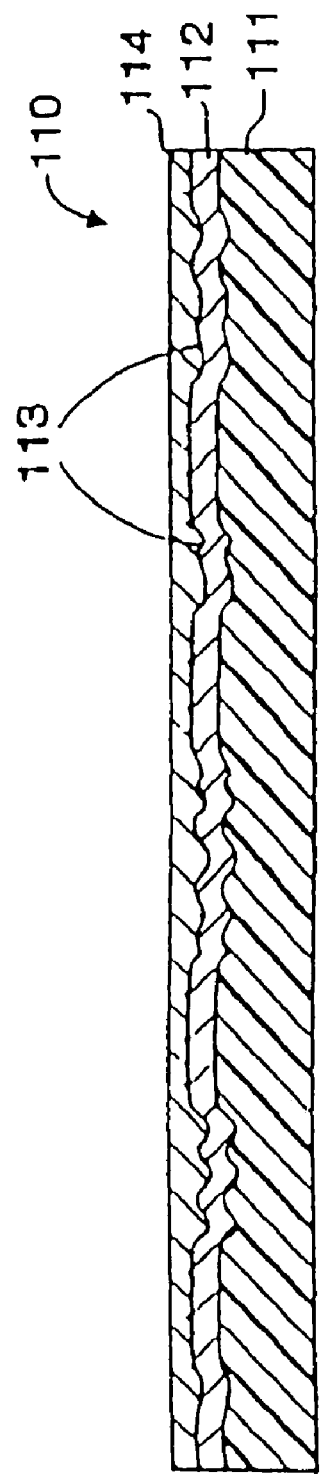
FIG. 9 shows a cross-section of an optically-readable data storage medium.

FIG. 9 shows a cross-section of an optically-readable data storage medium 110 which also can be encoded with such a machine-readable data, or set of instructions, which can be carried out by a system such as system 10 of FIG. 7. Medium 110 can be a conventional compact disk read only memory (CD-ROM) or a rewritable medium such as a magneto-optical disk that is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

The present invention permits the use of molecular design techniques to identify, select or design potential inhibitors of GSK-3, based on the structure of a substrate thereof. Such a predictive model is valuable in light of the high costs associated with the preparation and testing of the many diverse compounds that may possibly bind to GSK-3.

One skilled in the art may use the computer-assisted method of structure based drug design of GSK-3 inhibitors according to the present invention to design and screen chemical entities or fragments for their ability to mimic the structure of a peptide substrate of GSK-3. By using the 3D computer image of a peptide substrate of GSK-3, such as the p9CREB peptide substrate as a preferred embodiment, a potential GSK-3 inhibitor can be designed through rational drug design when 2D $^1$H NMR structural coordinate data of the GSK-3 peptide substrate is analyzed on a computer. A graphical display software program that creates an electronic file and then visualizes the electronic file on a computer capable of representing the electronic file as a 3D image aids in the design of a chemical compound that is assayed by contacting the compound with GSK-3 and detecting whether or not the chemical compound is a potential inhibitor that inhibits the phosphorylation activity of GSK-3. A chemical compound that inhibits GSK-3 activity is selected as a potential drug.

This process may additionally include, for example, a visual inspection of the structure of the potential GSK-3 inhibitor in relation to a catalytic binding pocket of GSK-3 on the computer screen based on, e.g., the structure coordinates of the p9CREB peptide substrate of GSK-3 as shown in Table 3 or other coordinates which define a similar shape generated from the machine-readable storage medium. The crystal structure determination of GSK-3β was reported by Dajani et al., (2001) and ter Haar et al. (2001). Selected fragments or chemical entities may then be positioned in a variety of orientations, or docked, within a catalytic binding pocket of GSK-3. Docking may be accomplished using software such as Quanta and Sybyl, followed by energy minimization and molecular dynamics with standard molecular mechanics force fields, such as CHARMM and AMBER.

Once a potential inhibitor is identified, it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential inhibitor may be synthesized de novo. As mentioned above, the de novo synthesis of one or even a relatively small group of specific compounds is reasonable in the art of drug design. The prospective drug can be physically tested to confirm its projected activity. For example, if the activity sought for such a potential inhibitor is its ability to inhibit the phosphorylation activity of GSK-3, the potential inhibitor can be placed into any standard phosphorylation assay, such as described below, to test its effect on GSK-3 activity.

Specialized computer programs may also assist in the process of selecting chemical entities. These include:
  1. GRID (Goodford, 1985), which is available from Oxford University, Oxford, UK.
  2. MCSS (Miranker et al, 1991), which is available from Molecular Simulations, San Diego, Calif.
  3. AUTODOCK (Goodsell et al, 1990), which is available from Scripps Research Institute, La Jolla, Calif.
  4. DOCK (Kuntz et al, 1982), which is available from University of California, San Francisco, Calif.

Once suitable chemical entities or fragments have been selected, they can be designed or assembled into a single compound or complex. Assembly may be preceded by visual inspection of the relationship of the chemical entities or the fragments to each other on the 3-dimensional image displayed on a computer screen in relation to the structure coordinates of GSK-3. This would be followed by manual model building using software such as Quanta or Sybyl (Tripos Associates, St. Louis, Mo.). Useful programs to aid one of skill in the art in connecting the individual chemical entities or fragments include:
  1. CAVEAT (Bartlett et al, 1989; Lauri et al, 1994), which is available from the University of California, Berkeley, Calif.
  2. 3D Database systems, such as ISIS (MDL Information Systems, San Leandro, Calif.). This area is reviewed in Martin, 1992.
  3. HOOK (Eisen et al, 1994), which is available from Molecular Simulations, San Diego, Calif.

Instead of proceeding to build an inhibitor of a catalytic binding pocket of GSK-3 in a step-wise fashion one fragment or chemical entity at a time, GSK-3 inhibitors may be designed as a whole or "de novo" using either an empty binding site or optionally including some portion(s) of a known inhibitor(s). There are many de novo ligand design methods including:
  1. LUDI (Bohm, 1992), which is available from Molecular Simulations Incorporated, San Diego, Calif.
  2. LEGEND (Nishibata et al, 1991), which is available from Molecular Simulations Incorporated, San Diego, Calif.
  3. LeapFrog (available from Tripos Associates, St. Louis, Mo.).
  4. SPROUT (Gillet et al, 1993), which is available from the University of Leeds, UK.

Other molecular modeling techniques may also be employed in accordance with this invention (see, e.g., Cohen et al, 1990; Navia et al, 1992; Balbes et al, 1994; Guida, 1994).

Once a compound has been designed or selected by the above methods, the efficiency with which that chemical entity may bind to a catalytic binding of GSK-3 involved in the phosphorylation activity of GSK-3 pocket may be tested and optimized by computational evaluation. For example, an effective GSK-3 catalytic binding pocket inhibitor must preferably demonstrate a relatively small difference in energy between its bound and free states (i.e., a small deformation energy of binding). Thus, the most efficient GSK-3 binding pocket inhibitors should preferably be designed with a deformation energy of binding of not greater than about 10 kcal/mole, more preferably, not greater than 7 kcal/mole. GSK-3 catalytic binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected based on GSK-3 peptide substrates and on binding to a GSK-3 catalytic binding pocket may be further computationally optimized so that in its bound state it would preferably lack repulsive electrostatic interaction with the GSK-3 and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 99, revision C (M. J. Frisch, Gaussian, Inc., Pittsburgh, Pa., ©1995); AMBER, version 4.1 (P. A. Kollman, University of California at San Francisco, ©1995); QUANTA/CHARMM (Molecular Simulations, Inc., San Diego, Calif. ©1995); Insight II/Discover (Molecular Simulations, Inc., San Diego, Calif. ©1995); DelPhi (Molecular Simulations, Inc., San Diego, Calif. ©1995); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that mimic a peptide substrate of GSK-3 and can bind in whole, or in part, to a GSK-3 binding pocket. In this screening, the quality of fit of such entities to the binding site may be judged either by shape complementarily or by estimated interaction energy (Meng et al, 1992).

According to another embodiment, the present invention provides peptide inhibitors of the phosphorylation activity of GSK-3 produced and identified by the method set forth above.

The details of one or more embodiments of the invention are set forth in the accompanying description above. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs.

odologies. Table 1 summarizes the peptides that were synthesized and tested for their ability to inhibit GSK-3. The peptides were patterned after two known substrates of GSK-3, CREB (cAMP response element binding protein) (Fiol et al, 1994), and heat shock factor-1 (HSF-1) (Chu et al, 1996). As illustrated in peptide #1, two serine sites are important in the recognition process, a phosphorylated serine (2) and the serine phosphorylated by the enzyme (1), the two serine being separated by 3 amino acids. This recognition process is also demonstrated in peptide #3 (p9CREB), which is the same as peptide #1 shortened to 9 amino acids, which peptide is also a good substrate of GSK-3 (see Eldar-Finkelman et al, 1997; and Hallstrom et al, 1998). The presence of phosphorylated serine (site 2) is absolutely required for the enzyme activity. This is demonstrated by a non-phosphorylated CREB peptide (#2) that is not a substrate. Furthermore, replacement of site 2 by glutamic acid which mimics a phosphorylated residue, does not convert this peptide to a substrate (#4). However, replacement of site 1 to alanine converts the peptide to a competitive inhibitor (peptide #5 see also FIG. 2). Similarly, when site 1 of the phosphopeptide derived from HSF-1 is replaced with alanine (#7), the peptide becomes a competitive inhibitor. Replacement of glutamic acid located downstream of the site 1 of peptide #7 (bold) improves the inhibitory effect of this peptide (#8). Thus, glutamic acid is important for enzyme-substrate/inhibitor interaction. The data from the laboratory of the present inventor also indicate that at least 4 amino acids downstream of serine site 1 must be present. Otherwise this peptide does not inhibit the enzyme (peptide#6, 9, 10, 11).

TABLE 1

Synthetic Peptides Are Listed and Their Kinetic Properties Are Indicated

| Peptide # | SEQ ID NO | # Residues | Property |
|---|---|---|---|
|         1  2 | | | A substrate |
| 1. KRREILSRRPS(p)YR | 1 | 13 | Derived from CREB protein |
| 2. KRREILSRRPSYR | 2 | 13 | Not a substrate |
| 3. ILSRRPS(p)YR | 3 | 9 | A substrate |
| 4. ILSRRPEYR | 4 | 9 | Neither a substrate nor an inhibitor |
| 5. KRREILARRPS(p)YR | 5 | 13 | An inhibitor $IC_{50}$ = 330 $\mu$M |
| 6. EILARRPS(p)Y | 6 | 9 | Does not inhibit |
| 7. KFEPPAPPQS(p)P | 7 | 11 | (patterned after HSF-1 protein) An inhibitor ($IC_{50}$ = 250 $\mu$M) |
| 8. KEAPPAPPQS(p)P | 8 | 11 | An inhibitor ($IC_{50}$ = 190 $\mu$M) |
| 9. EPPARRE | 9 | 7 | Does not inhibit |
| 10. EPPAPR | 10 | 6 | Does not inhibit |
| 11. PAPPQS(p)P | 11 | 7 | Does not inhibit |

The following Examples are presented in order to more fully illustrate the preferred embodiments of the invention. These Examples should in no way be construed as limiting the scope of the invention, as defined by the appended claims.

EXAMPLE 1

Synthesis of a GSK-3 Peptide Inhibitor

Small, synthetic peptide inhibitors, which are highly specific for GSK-3, were synthesized as described below. The peptides were synthesized according to standard meth-

EXAMPLE 2

Selective Inhibition of GSK-3 by a Peptide Inhibitor

Inhibition of Substrate Phosphorylation Activity of GSK-3

The inhibition of GSK-3 activity by a small, synthetic peptide inhibitor synthesized as described above in Example 1, was tested by in vitro kinase assay. Peptide inhibitor #5 (see Table 1) is a 13 amino acid synthetic peptide having the sequence KRREILARRPS(p)YR (SEQ ID NO:5), where S(p)=phosphoserine, and A represents the Ser to Ala substitution at the GSK-3 phosphorylation site.

Inhibition of GSK-3 by the peptide inhibitor #5 was determined by performing in vitro kinase assays of GSK-3 with a peptide substrate and determination of $^{32}$P incorporation into the substrate. In vitro kinase assays were performed utilizing purified recombinant rabbit GSK-3 using the method of Eldar-Finkelman et al (1997), a peptide substrate PGS-1 peptide (see Hallstrom et al, 1998), various concentrations of the peptide inhibitor, and $^{32}$P-γATP. The assay mixture contained: 0.5 μl GSK-3 (0.5 μg), 50 mM Tris, 10 mM MgAc, 0.01% β-mercaptoethanol, 50 μM $^{32}$P-γATP (0.25 μCi/assay), and 50 μM PSG-1 peptide. Reaction mixtures were incubated at 30° C. for 15 minutes, then spotted on p81 phosphocellulose paper squares, washed with 100 mM phosphoric acid, dried and counted for radioactivity.

The results of this representative in vitro inhibition assay of GSK-3 with an exemplary peptide inhibitor, peptide #5, are shown in FIG. 1. These results show the strong inhibition of GSK-3 phosphorylation of its substrate by the peptide inhibitor ($IC_{50}$=150 μM). Similar results were obtained when a different peptide substrate, p9CREB, was used.

Figure 2A:
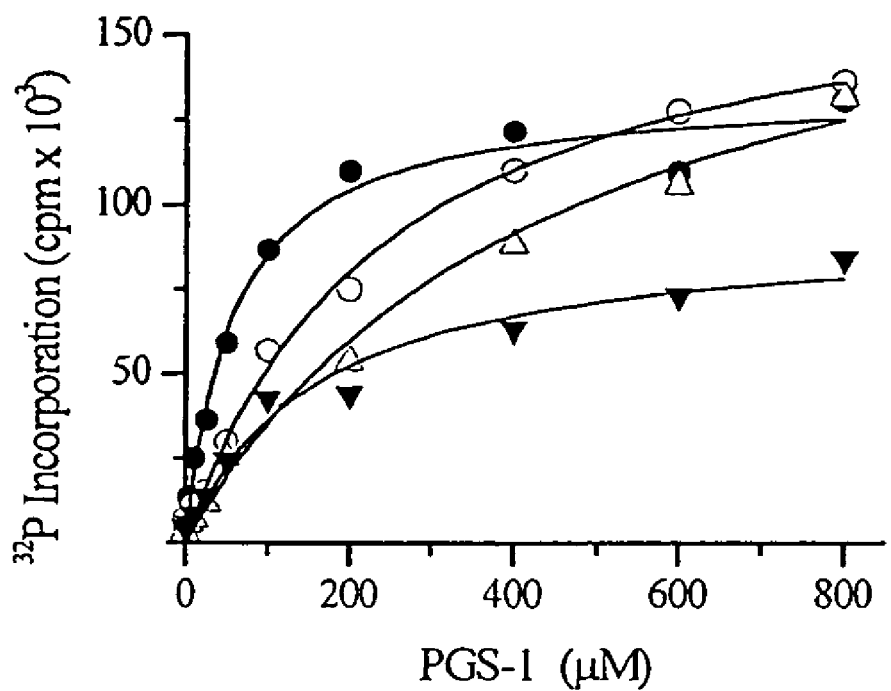
FIGS. 2A–2B indicate that peptide inhibitors are competitive inhibitors. Purified GSK-3 was incubated with 200 µM peptides inhibitors together with PGS-1 substrate and $^{32}$P-labeled ATP. The reactions were incubated at 30° C. for 15 minutes. Reactions were spotted on p81 (phosphocellulose papers) washed with phosphoric acid and counted for radioactivity. Results are presented as $^{32}$P-incorporation into peptide (FIG. 2A). Filled circles—no peptide, hollow circles—peptide #5, hollow triangles—peptide #7, filled triangles—peptide #8. Lineweaver-Burk plots of data obtained from peptide #8 are shown in FIG. 2B.
Figure 2B:
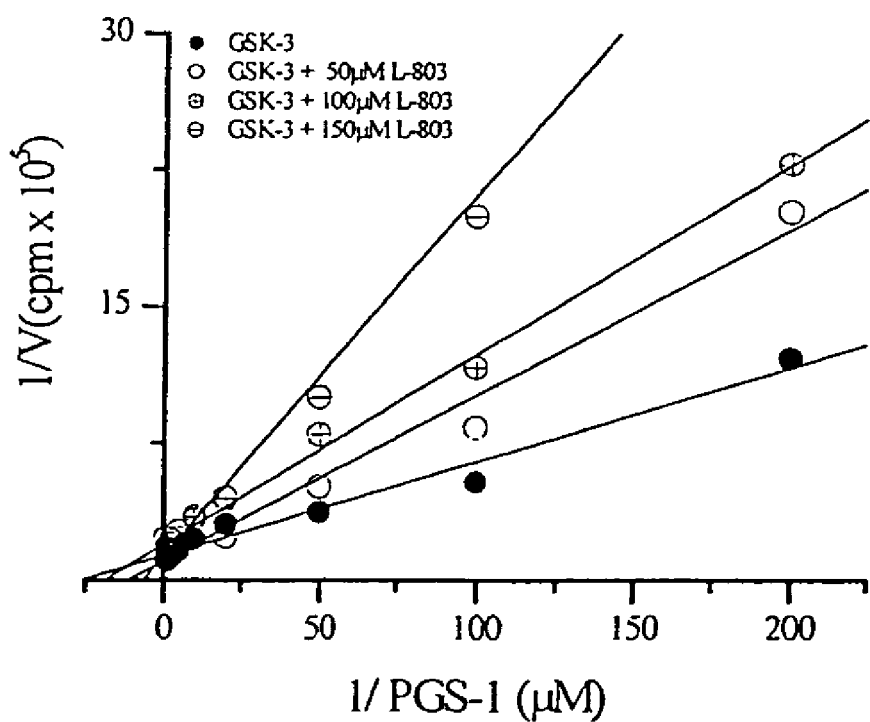

The inhibition of GSK-3 by peptides #5, 7 and 8 is shown in FIG. 2. Lineweaver-Burk plots revealed that all three peptides are competitive inhibitors. The data also suggest that peptide #8 is the best inhibitor. Ki value was determined for peptide #8 as 76 μM.

EXAMPLE 3

The Effect of Peptide Inhibitor on Glycogen Synthase in Intact Cells

Figure 3:
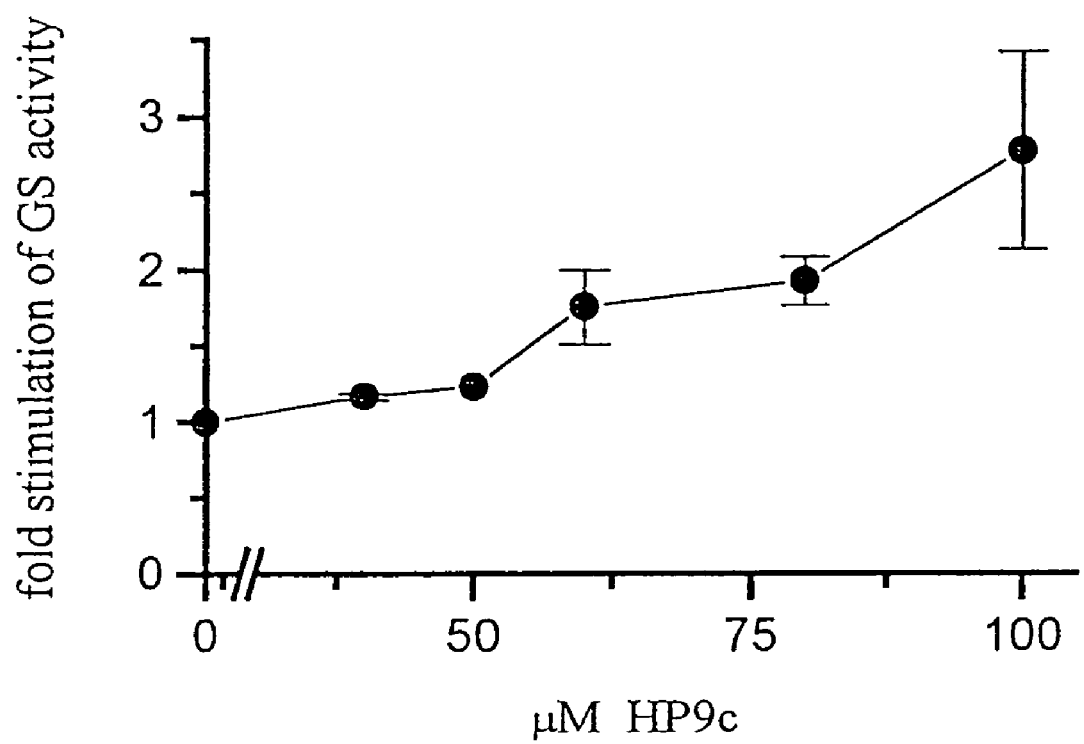
FIG. 3 shows the effect of peptide inhibitor on glycogen synthase activity in intact cells. 293 cells were treated with HP9c for 2.5 hours. Cells were lysed and GS activity was determined as described (Eldar-Finkelman et al, 1996). Results present fold stimulation of GS activity observed in control cells treated with DMSO vehicle. Data are mean±SE of 3 independent experiments.

The present inventor examined whether the peptide inhibitors are capable of inhibiting GSK-3 activity in intact cells. There is a substantial evidence that insulin-activation of glycogen synthase (GS) is via inhibition of GSK-3. Peptide #5 was, therefore, tested to see if it enhanced GS activity in intact cells. In order to improve the delivery of the peptide into cells, synthesized peptide #5 was linked to a hydrophobic cell permeable peptide (16 amino acids; Hawiger, 1997), termed here HP9c. 293 cells were treated with increased concentrations of HP9c, and GS activity was measured as previously described (Eldar-Finkelman et al, 1996). Treatment of cells with the peptides resulted in increased basal GS activity. The effective peptide concentrations ranged between 60–100 μM (FIG. 3).

Figure 4:
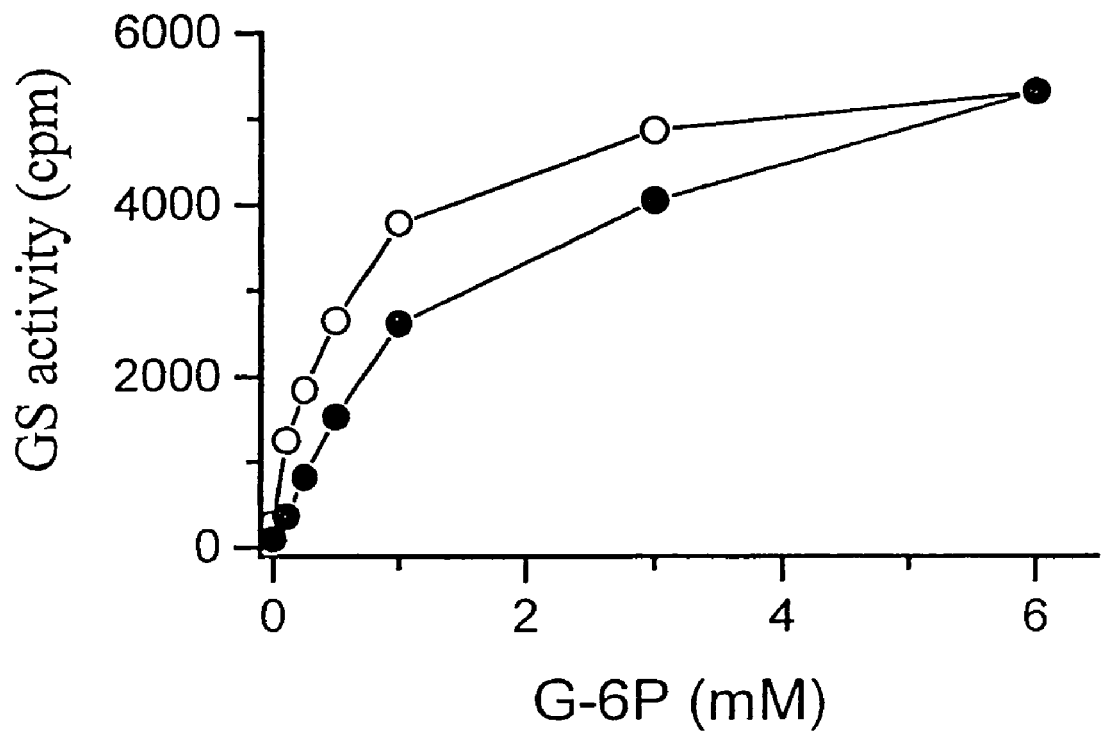
FIG. 4 shows that peptide inhibitor HP9c enhances allosteric activation of glycogen synthase by G6P. 293 cells were treated with 60 µM HP9c for 2.5 hours. Glycogen synthase activity was assayed in cell extracts in the presence of varied concentration of G6P as indicated. G6P dose response curve of one representative experiment is presented. Each point represents an average of duplicated samples. Filled circles—control. Hollow circles—peptide treated cells.

Phosphorylation of GS by GSK-3 also enhances GS sensitivity to its allosteric regulator glucose 6 phosphate (G6P). This effect was shown in vitro and in intact cells in the laboratory of the present inventor. Thus, if GSK-3 is inhibited in intact cells, then activation of GS by G6P should enhanced. FIG. 4 shows that treatment of cells with HP9c peptide inhibitor resulted in enhanced activation of GS by G6P. In this experiment, G6P dose response activation of GS that was isolated from peptide-treated and non-treated cells was examined. Results show that GS from treated cells (hollow circles) is better activated by G6P as compared to control.

EXAMPLE 4

Molecular Basis for Drug Design of GSK-3 Inhibitors

Recognition of substrates by GSK-3 is unconventional in that it usually requires prior phosphorylation. GSK-3 phosphorylates serine in the motif $S^1XXXS^2$ (p) where $S^2$(p) is a phosphorylated serine, $S^1$ is the serine site phosphorylated by GSK-3, and X=any amino acid. Based on this feature, a novel class of peptide inhibitors that inhibit GSK-3 with IC50 of 100–200 μM according to the present invention was designed. The next step was to determine the structure of a phosphorylated peptide substrate in order to develop further selective inhibitors for GSK-3.

Figure 5:
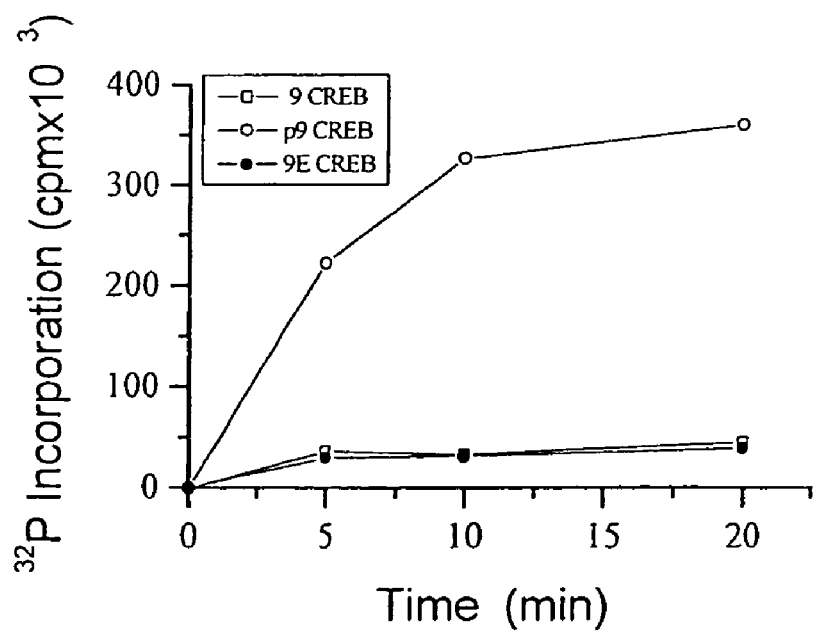
FIG. 5 shows a graph of a time course phosphorylation of CREB peptides indicating that only the phosphorylated peptide served as a substrate for the enzyme. Peptides were incubated with GSK-3 enzyme in a mixture containing 100 mM Mg$^{++}$ and 10 µM $^{32}$P-γATP. Reactions were spotted on p81 papers and counted for radioactivity. The results present the incorporation of phosphate into peptides.

A small phospho-peptide patterned after a CREB substrate, denoted p9CREB, and two additional peptides, a non-phosphorylated peptide, 9CREB, and a variant where $S^1$ was replaced with glutamic acid (which is thought to mimic a charged group), 9ECREB, were used in these studies and are listed in Table 2. Time course analyses of peptide phosphorylation by GSK-3 confirmed that only the phosphorylated peptide, p9CREB, was a substrate for GSK-3, while 9CREB and 9ECREB completely failed to be phosphorylated by GSK-3 (FIG. 5). Thus, phosphorylated serine is an absolute requirement for GSK-3.

TABLE 2

| Peptide | Sequence | SEQ ID NO: |
| --- | --- | --- |
| p9CREB | ILSRRPS(p)YR | 3 |
| 9CREB | ILSRRPSYR | 12 |
| 9ECREB | ILSRRPEYR | 14 |

Figure 6A:
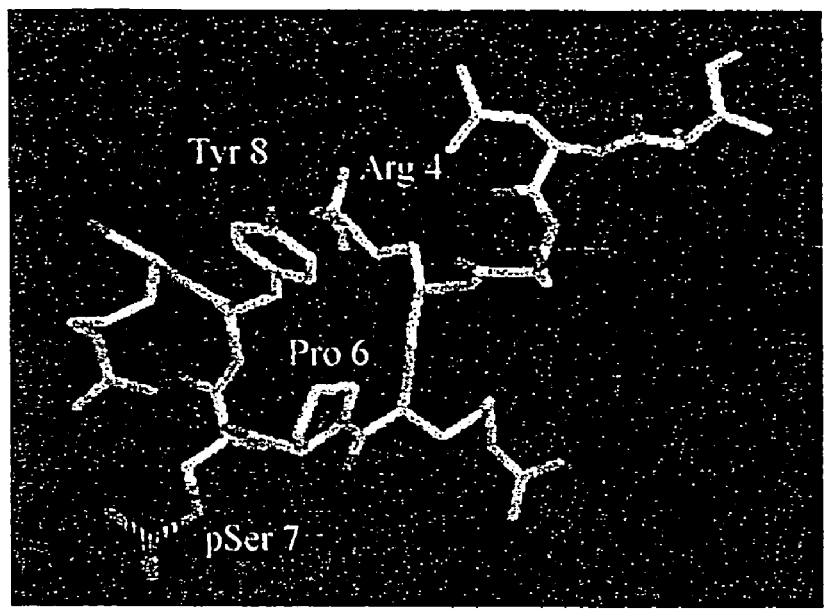
FIGS. 6A and 6B show three dimensional computer images of the structure of the phosphorylated peptide p9CREB (FIG. 6A) and its non-physphorylated version (FIG. 6B), as derived from 2D $^1$H NMR studies. Phosphorylation at serine 7 (Ser 7) imposes a 'turn' of the peptide backbone, bringing Tyr 8 closer to Arg 4 forming a 'loop like' structure. As a result, the phosphorylated serine is stretched out of the loop. This structure provides an explanation for the substrate specificity of GSK-3. Peptide backbone-light gray, nitrogen-medium gray, oxygen-dark gray, phosphate-striped. Hydrogen atoms are omitted in this presentation.
Figure 6B:
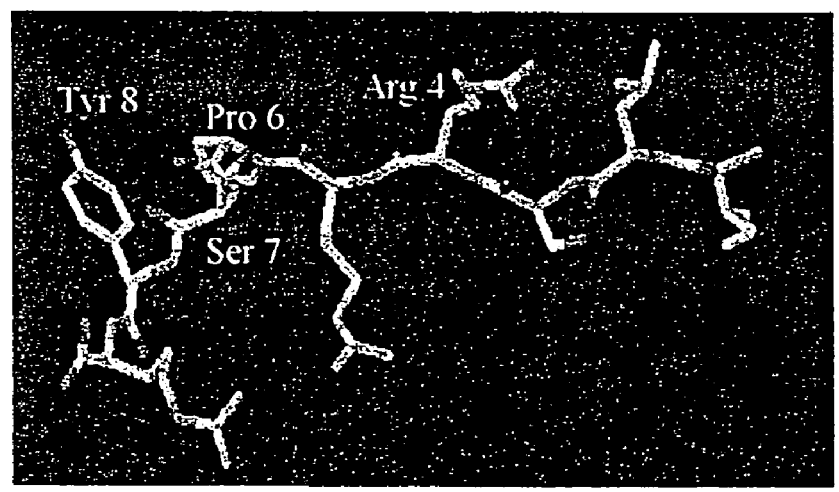

The laboratory of the present inventor and a colleague determined the 3D structure of p9CREB (FIG. 6A), 9CREB (FIG. 6B) and 9ECREB (not shown) by 2D $^1$H NMR spectroscopy using the following procedures:

NMR Spectroscopy and Structure Calculations

For the structural studies, a solution of each peptide was prepared by dissolving lyophilized powder in water containing 10% $D_2O$. 2D NMR spectra were acquired at the $^1$H proton frequency of 600.13 MHz on a Bruker Avance DMX spectrometer. The carrier frequency was set on the water signal and it was suppressed by applying either a WATERGATE method and by low-power irradiation during the relaxation period. The experimental temperature (280 K) was optimized in order to reduce population averaging due to the fast exchange at more ambient temperatures, while preserving the best possible spectral resolution. All experiments were carried out in the phase sensitive mode (TPPI or States-TPPI) and recorded with a spectral width of 12 ppm, with 4K real $t_2$ data points and 512 $t_1$-increments. Two-dimensional homonuclear data collected included TOCSY using a MLEV pulse sequence with a mixing time of 150 msec, and NOESY experiments with mixing times ranging between 100 and 750 msecs. Typically, the relaxation delays were 1.5 and 2.0 sec in TOCSY and NOESY experiments, respectively. In the ROESY measurements, the duration of the spin-lock was set to 400 msec with a power of 3.4 KHz. All spectra were calibrated versus tetramethylsilane.

The data was processed using Bruker XWINNMR software (Bruker Analytische Messtechnik, GmbH, version 2.7). All data processing, calculations and analysis were done on Silicon Graphics workstations (INDY R4000 and INDIGO2 R10000). Zero filling of the indirect dimension and apodization of the free induction decay by a shifted squared-sine window function on both dimensions were applied prior to Fourier transformation to enhance spectral resolution. The spectra were further phase-corrected by applying an automatic polynomial baseline correction developed by Bruker.

Resonance assignment was based on the TOCSY and NOESY spectra measured at the same experimental conditions, according to the sequential assignment methodology developed by Wuthrich using the Bruker software program AURELIA (Bruker Analytic GmbH, version 2.7).

NOE Measurements and Experimental Distance Restraints

The NOE distance restraints were derived from NOESY spectra recorded at 450 msec. This optimal mixing time was determined for the p9CREB peptide sample by comparing the NOE signal intensities in a series of experiments with mixing times varying from 100 msec to 750 msec. The chosen mixing time gave maximal NOE buildup with no significant contribution from spin diffusion. This value was used for the non-phosphorylated analog experiment in order to maintain identical experimental conditions. Integrated peak volumes were converted into distance restraints using a $r^{-6}$ dependency and the known distance of 2.47 Å between the two adjacent protons of the tyrosine aromatic ring was used for calibration. The restraints were classified into strong (1.8–2.5 Å), medium (1.8–3.5 Å) and weak (1.8–5.0 Å). An empirical correction of 0.5 Å was added to the upper bound for restraints involving methyl groups.

The structures were calculated by hybrid distance geometry—dynamical simulated annealing using XPLOR (version 3.856). The NOE energy was introduced as a square-well potential with a constant force constant of 50 Kcal/mol·Å$^2$. Simulated annealing consisted of 1500 3 fsec steps at 1000 K and 3000 1 fsec steps during cooling to 300 K. Finally, the structures were minimized using conjugate gradient energy minimization for 4000 iterations. INSIGHTII (Molecular Modeling System version 97.0, Molecular Simulations, Inc.) was used for visualization and analysis of the NMR-derived structures. Their quality was assessed using PROCHECK.

Table 3 presents the structural coordinate data that can be used for inputting into structure analysis software for visualization of the 3D structures.

From the 3D structures, it was observed that only the phosphorylated peptide has a defined structural conformation. Phosphorylation imposed a significant "turn" of the peptide backbone bringing Tyr 8 and Arg 4 closer, forming a 'loop structure' for p9CREB. The phosphorylated residue is pointing out of the loop. This conformation minimizes on the one hand interference of positively charged residues (Arg 4 and Arg 5) with the catalytic binding pocket of the enzyme, and on the other hand, makes the phosphorylated serine readily accessible to the enzyme. The structure analysis presented here provides an explanation for the unique substrate recognition of GSK-3. Based on the fact that phosphorylated peptides inhibit GSK-3 as shown in Example 2, the design of small molecules that mimic the structure presented here provides a method for obtaining potential selective inhibitors for GSK-3.

EXAMPLE 5

Treating a Patient with NIDDM

A patient is diagnosed in the early stages of non-insulin dependent diabetes mellitus. A peptide inhibitor of GSK-3 in accordance with the present invention is formulated in an enteric capsule. The patient is directed to take one tablet after each meal for the purpose of stimulating the insulin signaling pathway, and thereby controlling glucose metabolism to levels that obviate the need for administration of exogenous insulin.

EXAMPLE 6

Treating a Patient with Alzheimer's Disease

A patient is diagnosed with Alzheimer's disease. The patient is administered a selective peptide inhibitor of the present invention, which inhibits GSK-3-mediated tau hyperphosphorylation prepared in a formulation that crosses the blood/brain barrier. The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the inhibitor is adjusted as necessary to reduce the presence of the phosphorylated forms of tau protein.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

TABLE 3

```
REMARK FILENAME="refine_1_4.pdb"
REMARK ================================================================
REMARK overall,bonds,angles,improper,vdw,noe,cdih
REMARK energies: 49.6206, 2.76302, 18.089, 2.9318, 0.894357, 24.9424,
$CDIH
REMARK ================================================================
REMARK bonds,angles,impropers,noe,cdih
REMARK rms-d: 4.019702E−03,0.622994,0.465061,9.195132E−02,0
REMARK ================================================================
REMARK noe, cdih
REMARK violations.: 0, 0
REMARK ================================================================
REMARK DATE: 27-Apr-00 08:12:42      created by user: orish
```

| | | | | | | | | | |
|---|---|---|---|---|---|---|---|---|---|
| ATOM | 1  | CA   | ILE | 1 | 11.861 | −0.265 | −1.755 | 1.00 | 0.00 |
| ATOM | 2  | HA   | ILE | 1 | 11.773 | 0.710  | −1.305 | 1.00 | 0.00 |
| ATOM | 3  | CB   | ILE | 1 | 11.788 | −0.143 | −3.278 | 1.00 | 0.00 |
| ATOM | 4  | HB   | ILE | 1 | 10.810 | 0.216  | −3.564 | 1.00 | 0.00 |
| ATOM | 5  | CG1  | ILE | 1 | 12.034 | −1.514 | −3.911 | 1.00 | 0.00 |
| ATOM | 6  | HG11 | ILE | 1 | 12.789 | −2.041 | −3.347 | 1.00 | 0.00 |
| ATOM | 7  | HG12 | ILE | 1 | 12.368 | −1.385 | −4.930 | 1.00 | 0.00 |
| ATOM | 8  | CG2  | ILE | 1 | 12.852 | 0.841  | −3.766 | 1.00 | 0.00 |
| ATOM | 9  | HG21 | ILE | 1 | 13.794 | 0.326  | −3.880 | 1.00 | 0.00 |
| ATOM | 10 | HG22 | ILE | 1 | 12.963 | 1.638  | −3.045 | 1.00 | 0.00 |
| ATOM | 11 | HG23 | ILE | 1 | 12.551 | 1.256  | −4.717 | 1.00 | 0.00 |
| ATOM | 12 | CD1  | ILE | 1 | 10.735 | −2.319 | −3.895 | 1.00 | 0.00 |
| ATOM | 13 | HD11 | ILE | 1 | 10.871 | −3.209 | −3.300 | 1.00 | 0.00 |
| ATOM | 14 | HD12 | ILE | 1 | 10.472 | −2.596 | −4.905 | 1.00 | 0.00 |
| ATOM | 15 | HD13 | ILE | 1 | 9.945  | −1.718 | −3.469 | 1.00 | 0.00 |
| ATOM | 16 | C    | ILE | 1 | 10.762 | −1.195 | −1.232 | 1.00 | 0.00 |
| ATOM | 17 | O    | ILE | 1 | 10.856 | −2.402 | −1.334 | 1.00 | 0.00 |
| ATOM | 18 | N    | ILE | 1 | 13.205 | −0.849 | −1.475 | 1.00 | 0.00 |
| ATOM | 19 | HT1  | ILE | 1 | 13.115 | −1.875 | −1.335 | 1.00 | 0.00 |
| ATOM | 20 | HT2  | ILE | 1 | 13.599 | −0.414 | −0.615 | 1.00 | 0.00 |
| ATOM | 21 | HT3  | ILE | 1 | 13.839 | −0.665 | −2.278 | 1.00 | 0.00 |
| ATOM | 22 | N    | LEU | 2 | 9.722  | −0.643 | −0.667 | 1.00 | 0.00 |
| ATOM | 23 | HN   | LEU | 2 | 9.666  | 0.337  | −0.591 | 1.00 | 0.00 |
| ATOM | 24 | CA   | LEU | 2 | 8.619  | −1.500 | −0.136 | 1.00 | 0.00 |
| ATOM | 25 | HA   | LEU | 2 | 8.809  | −2.544 | −0.349 | 1.00 | 0.00 |
| ATOM | 26 | CB   | LEU | 2 | 8.630  | −1.265 | 1.375  | 1.00 | 0.00 |
| ATOM | 27 | HB1  | LEU | 2 | 7.626  | −1.058 | 1.714  | 1.00 | 0.00 |
| ATOM | 28 | HB2  | LEU | 2 | 9.269  | −0.424 | 1.604  | 1.00 | 0.00 |
| ATOM | 29 | CG   | LEU | 2 | 9.156  | −2.514 | 2.083  | 1.00 | 0.00 |
| ATOM | 30 | HG   | LEU | 2 | 9.725  | −3.111 | 1.384  | 1.00 | 0.00 |
| ATOM | 31 | CD1  | LEU | 2 | 10.056 | −2.100 | 3.249  | 1.00 | 0.00 |
| ATOM | 32 | HD11 | LEU | 2 | 11.090 | −2.148 | 2.940  | 1.00 | 0.00 |
| ATOM | 33 | HD12 | LEU | 2 | 9.897  | −2.770 | 4.081  | 1.00 | 0.00 |
| ATOM | 34 | HD13 | LEU | 2 | 9.816  | −1.091 | 3.548  | 1.00 | 0.00 |
| ATOM | 35 | CD2  | LEU | 2 | 7.977  | −3.332 | 2.615  | 1.00 | 0.00 |
| ATOM | 36 | HD21 | LEU | 2 | 7.730  | −3.000 | 3.613  | 1.00 | 0.00 |
| ATOM | 37 | HD22 | LEU | 2 | 8.246  | −4.378 | 2.640  | 1.00 | 0.00 |
| ATOM | 38 | HD23 | LEU | 2 | 7.123  | −3.195 | 1.968  | 1.00 | 0.00 |
| ATOM | 39 | C    | LEU | 2 | 7.279  | −1.067 | −0.736 | 1.00 | 0.00 |
| ATOM | 40 | O    | LEU | 2 | 7.213  | −0.161 | −1.544 | 1.00 | 0.00 |
| ATOM | 41 | N    | SER | 3 | 6.209  | −1.707 | −0.349 | 1.00 | 0.00 |
| ATOM | 42 | HN   | SER | 3 | 6.283  | −2.435 | 0.304  | 1.00 | 0.00 |
| ATOM | 43 | CA   | SER | 3 | 4.875  | −1.331 | −0.898 | 1.00 | 0.00 |
| ATOM | 44 | HA   | SER | 3 | 4.861  | −0.288 | −1.173 | 1.00 | 0.00 |
| ATOM | 45 | CB   | SER | 3 | 4.700  | −2.201 | −2.142 | 1.00 | 0.00 |
| ATOM | 46 | HB1  | SER | 3 | 5.077  | −1.671 | −3.007 | 1.00 | 0.00 |
| ATOM | 47 | HB2  | SER | 3 | 3.655  | −2.421 | −2.286 | 1.00 | 0.00 |
| ATOM | 48 | OG   | SER | 3 | 5.414  | −3.418 | −1.967 | 1.00 | 0.00 |
| ATOM | 49 | HG   | SER | 3 | 4.796  | −4.082 | −1.654 | 1.00 | 0.00 |
| ATOM | 50 | C    | SER | 3 | 3.777  | −1.630 | 0.126  | 1.00 | 0.00 |
| ATOM | 51 | O    | SER | 3 | 3.504  | −2.771 | 0.442  | 1.00 | 0.00 |
| ATOM | 52 | N    | ARG | 4 | 3.145  | −0.613 | 0.646  | 1.00 | 0.00 |
| ATOM | 53 | HN   | ARG | 4 | 3.380  | 0.300  | 0.375  | 1.00 | 0.00 |
| ATOM | 54 | CA   | ARG | 4 | 2.063  | −0.839 | 1.649  | 1.00 | 0.00 |
| ATOM | 55 | HA   | ARG | 4 | 1.545  | −1.766 | 1.443  | 1.00 | 0.00 |
| ATOM | 56 | CB   | ARG | 4 | 2.784  | −0.921 | 3.001  | 1.00 | 0.00 |
| ATOM | 57 | HB1  | ARG | 4 | 2.113  | −0.610 | 3.789  | 1.00 | 0.00 |
| ATOM | 58 | HB2  | ARG | 4 | 3.648  | −0.270 | 2.990  | 1.00 | 0.00 |
| ATOM | 59 | CG   | ARG | 4 | 3.234  | −2.362 | 3.257  | 1.00 | 0.00 |
| ATOM | 60 | HG1  | ARG | 4 | 4.312  | −2.395 | 3.326  | 1.00 | 0.00 |
| ATOM | 61 | HG2  | ARG | 4 | 2.906  | −2.991 | 2.444  | 1.00 | 0.00 |
| ATOM | 62 | CD   | ARG | 4 | 2.627  | −2.865 | 4.571  | 1.00 | 0.00 |
| ATOM | 63 | HD1  | ARG | 4 | 1.720  | −2.327 | 4.798  | 1.00 | 0.00 |
| ATOM | 64 | HD2  | ARG | 4 | 3.341  | −2.763 | 5.378  | 1.00 | 0.00 |
| ATOM | 65 | NE   | ARG | 4 | 2.321  | −4.302 | 4.326  | 1.00 | 0.00 |
| ATOM | 66 | HE   | ARG | 4 | 1.389  | −4.605 | 4.292  | 1.00 | 0.00 |

TABLE 3-continued

| | | | | | | | | |
|---|---|---|---|---|---|---|---|---|
| ATOM | 67 | CZ | ARG | 4 | 3.292 | −5.157 | 4.155 | 1.00 | 0.00 |
| ATOM | 68 | NH1 | ARG | 4 | 4.516 | −4.825 | 4.463 | 1.00 | 0.00 |
| ATOM | 69 | HH11 | ARG | 4 | 4.710 | −3.915 | 4.830 | 1.00 | 0.00 |
| ATOM | 70 | HH12 | ARG | 4 | 5.259 | −5.481 | 4.333 | 1.00 | 0.00 |
| ATOM | 71 | NH2 | ARG | 4 | 3.038 | −6.344 | 3.677 | 1.00 | 0.00 |
| ATOM | 72 | HH21 | ARG | 4 | 2.100 | −6.599 | 3.441 | 1.00 | 0.00 |
| ATOM | 73 | HH22 | ARG | 4 | 3.782 | −7.000 | 3.546 | 1.00 | 0.00 |
| ATOM | 74 | C | ARG | 4 | 1.081 | 0.336 | 1.636 | 1.00 | 0.00 |
| ATOM | 75 | O | ARG | 4 | 1.468 | 1.482 | 1.752 | 1.00 | 0.00 |
| ATOM | 76 | N | ARG | 5 | −0.187 | 0.062 | 1.495 | 1.00 | 0.00 |
| ATOM | 77 | HN | ARG | 5 | −0.480 | −0.873 | 1.402 | 1.00 | 0.00 |
| ATOM | 78 | CA | ARG | 5 | −1.192 | 1.168 | 1.475 | 1.00 | 0.00 |
| ATOM | 79 | HA | ARG | 5 | −0.705 | 2.127 | 1.595 | 1.00 | 0.00 |
| ATOM | 80 | CB | ARG | 5 | −1.844 | 1.083 | 0.094 | 1.00 | 0.00 |
| ATOM | 81 | HB1 | ARG | 5 | −2.917 | 1.041 | 0.204 | 1.00 | 0.00 |
| ATOM | 82 | HB2 | ARG | 5 | −1.499 | 0.192 | −0.412 | 1.00 | 0.00 |
| ATOM | 83 | CG | ARG | 5 | −1.465 | 2.316 | −0.727 | 1.00 | 0.00 |
| ATOM | 84 | HG1 | ARG | 5 | −0.748 | 2.908 | −0.179 | 1.00 | 0.00 |
| ATOM | 85 | HG2 | ARG | 5 | −2.350 | 2.907 | −0.918 | 1.00 | 0.00 |
| ATOM | 86 | CD | ARG | 5 | −0.848 | 1.876 | −2.057 | 1.00 | 0.00 |
| ATOM | 87 | HD1 | ARG | 5 | −0.300 | 0.955 | −1.931 | 1.00 | 0.00 |
| ATOM | 88 | HD2 | ARG | 5 | −0.202 | 2.651 | −2.445 | 1.00 | 0.00 |
| ATOM | 89 | NE | ARG | 5 | −2.008 | 1.659 | −2.965 | 1.00 | 0.00 |
| ATOM | 90 | HE | ARG | 5 | −2.795 | 2.241 | −2.903 | 1.00 | 0.00 |
| ATOM | 91 | CZ | ARG | 5 | −1.977 | 0.695 | −3.845 | 1.00 | 0.00 |
| ATOM | 92 | NH1 | ARG | 5 | −0.857 | 0.392 | −4.441 | 1.00 | 0.00 |
| ATOM | 93 | HH11 | ARG | 5 | −0.022 | 0.898 | −4.225 | 1.00 | 0.00 |
| ATOM | 94 | HH12 | ARG | 5 | −0.834 | −0.347 | −5.115 | 1.00 | 0.00 |
| ATOM | 95 | NH2 | ARG | 5 | −3.067 | 0.035 | −4.127 | 1.00 | 0.00 |
| ATOM | 96 | HH21 | ARG | 5 | −3.925 | 0.267 | −3.670 | 1.00 | 0.00 |
| ATOM | 97 | HH22 | ARG | 5 | −3.043 | −0.704 | −4.801 | 1.00 | 0.00 |
| ATOM | 98 | C | ARG | 5 | −2.236 | 0.954 | 2.575 | 1.00 | 0.00 |
| ATOM | 99 | O | ARG | 5 | −2.260 | −0.078 | 3.214 | 1.00 | 0.00 |
| ATOM | 100 | N | PRO | 6 | −3.068 | 1.946 | 2.758 | 1.00 | 0.00 |
| ATOM | 101 | CA | PRO | 6 | −4.149 | 1.876 | 3.807 | 1.00 | 0.00 |
| ATOM | 102 | HA | PRO | 6 | −3.740 | 1.628 | 4.790 | 1.00 | 0.00 |
| ATOM | 103 | CB | PRO | 6 | −4.710 | 3.304 | 3.802 | 1.00 | 0.00 |
| ATOM | 104 | HB1 | PRO | 6 | −4.213 | 3.918 | 4.537 | 1.00 | 0.00 |
| ATOM | 105 | HB2 | PRO | 6 | −5.780 | 3.296 | 3.976 | 1.00 | 0.00 |
| ATOM | 106 | CG | PRO | 6 | −4.411 | 3.814 | 2.426 | 1.00 | 0.00 |
| ATOM | 107 | HG1 | PRO | 6 | −4.357 | 4.887 | 2.428 | 1.00 | 0.00 |
| ATOM | 108 | HG2 | PRO | 6 | −5.177 | 3.477 | 1.740 | 1.00 | 0.00 |
| ATOM | 109 | CD | PRO | 6 | −3.087 | 3.236 | 2.027 | 1.00 | 0.00 |
| ATOM | 110 | HD2 | PRO | 6 | −3.044 | 3.093 | 0.948 | 1.00 | 0.00 |
| ATOM | 111 | HD1 | PRO | 6 | −2.275 | 3.877 | 2.353 | 1.00 | 0.00 |
| ATOM | 112 | C | PRO | 6 | −5.282 | 0.893 | 3.432 | 1.00 | 0.00 |
| ATOM | 113 | O | PRO | 6 | −6.393 | 1.035 | 3.902 | 1.00 | 0.00 |
| ATOM | 114 | N | SER | 7 | −5.030 | −0.093 | 2.607 | 1.00 | 0.00 |
| ATOM | 115 | HN | SER | 7 | −4.145 | −0.207 | 2.235 | 1.00 | 0.00 |
| ATOM | 116 | CA | SER | 7 | −6.110 | −1.051 | 2.233 | 1.00 | 0.00 |
| ATOM | 117 | HA | SER | 7 | −5.833 | −1.603 | 1.348 | 1.00 | 0.00 |
| ATOM | 118 | CB | SER | 7 | −6.238 | −2.001 | 3.415 | 1.00 | 0.00 |
| ATOM | 119 | HB1 | SER | 7 | −6.552 | −2.972 | 3.057 | 1.00 | 0.00 |
| ATOM | 120 | HB2 | SER | 7 | −6.974 | −1.619 | 4.102 | 1.00 | 0.00 |
| ATOM | 121 | OG | SER | 7 | −4.984 | −2.104 | 4.077 | 1.00 | 0.00 |
| ATOM | 122 | HG | SER | 7 | −5.045 | −2.814 | 4.720 | 1.00 | 0.00 |
| ATOM | 123 | C | SER | 7 | −7.430 | −0.316 | 2.010 | 1.00 | 0.00 |
| ATOM | 124 | O | SER | 7 | −8.251 | −0.211 | 2.899 | 1.00 | 0.00 |
| ATOM | 125 | N | TYR | 8 | −7.643 | 0.184 | 0.831 | 1.00 | 0.00 |
| ATOM | 126 | HN | TYR | 8 | −6.966 | 0.078 | 0.127 | 1.00 | 0.00 |
| ATOM | 127 | CA | TYR | 8 | −8.925 | 0.904 | 0.559 | 1.00 | 0.00 |
| ATOM | 128 | HA | TYR | 8 | −9.535 | 0.924 | 1.451 | 1.00 | 0.00 |
| ATOM | 129 | CB | TYR | 8 | −8.533 | 2.329 | 0.179 | 1.00 | 0.00 |
| ATOM | 130 | HB1 | TYR | 8 | −9.278 | 2.738 | −0.498 | 1.00 | 0.00 |
| ATOM | 131 | HB2 | TYR | 8 | −7.570 | 2.317 | −0.324 | 1.00 | 0.00 |
| ATOM | 132 | CG | TYR | 8 | −8.466 | 3.172 | 1.458 | 1.00 | 0.00 |
| ATOM | 133 | CD1 | TYR | 8 | −7.422 | 4.091 | 1.648 | 1.00 | 0.00 |
| ATOM | 134 | HD1 | TYR | 8 | −6.664 | 4.205 | 0.901 | 1.00 | 0.00 |
| ATOM | 135 | CD2 | TYR | 8 | −9.451 | 3.035 | 2.465 | 1.00 | 0.00 |
| ATOM | 136 | HD2 | TYR | 8 | −10.261 | 2.331 | 2.352 | 1.00 | 0.00 |
| ATOM | 137 | CE1 | TYR | 8 | −7.360 | 4.861 | 2.815 | 1.00 | 0.00 |
| ATOM | 138 | HE1 | TYR | 8 | −6.553 | 5.566 | 2.952 | 1.00 | 0.00 |
| ATOM | 139 | CE2 | TYR | 8 | −9.379 | 3.809 | 3.629 | 1.00 | 0.00 |
| ATOM | 140 | HE2 | TYR | 8 | −10.134 | 3.702 | 4.394 | 1.00 | 0.00 |
| ATOM | 141 | CZ | TYR | 8 | −8.336 | 4.721 | 3.803 | 1.00 | 0.00 |
| ATOM | 142 | OH | TYR | 8 | −8.270 | 5.483 | 4.951 | 1.00 | 0.00 |
| ATOM | 143 | HH | TYR | 8 | −7.345 | 5.662 | 5.136 | 1.00 | 0.00 |
| ATOM | 144 | C | TYR | 8 | −9.680 | 0.230 | −0.587 | 1.00 | 0.00 |
| ATOM | 145 | O | TYR | 8 | −9.400 | 0.456 | −1.747 | 1.00 | 0.00 |

TABLE 3-continued

| | | | | | | | | | |
|---|---|---|---|---|---|---|---|---|---|
| ATOM | 146 | N | ARG | 9 | −10.639 | −0.592 | −0.266 | 1.00 | 0.00 |
| ATOM | 147 | HN | ARG | 9 | −10.848 | −0.751 | 0.681 | 1.00 | 0.00 |
| ATOM | 148 | CA | ARG | 9 | −11.423 | −1.283 | −1.334 | 1.00 | 0.00 |
| ATOM | 149 | HA | ARG | 9 | −11.870 | −0.561 | −1.999 | 1.00 | 0.00 |
| ATOM | 150 | CB | ARG | 9 | −10.408 | −2.140 | −2.099 | 1.00 | 0.00 |
| ATOM | 151 | HB1 | ARG | 9 | −9.528 | −1.554 | −2.314 | 1.00 | 0.00 |
| ATOM | 152 | HB2 | ARG | 9 | −10.849 | −2.477 | −3.027 | 1.00 | 0.00 |
| ATOM | 153 | CG | ARG | 9 | −10.015 | −3.354 | −1.253 | 1.00 | 0.00 |
| ATOM | 154 | HG1 | ARG | 9 | −10.141 | −3.120 | −0.206 | 1.00 | 0.00 |
| ATOM | 155 | HG2 | ARG | 9 | −8.982 | −3.606 | −1.444 | 1.00 | 0.00 |
| ATOM | 156 | CD | ARG | 9 | −10.907 | −4.543 | −1.618 | 1.00 | 0.00 |
| ATOM | 157 | HD1 | ARG | 9 | −11.932 | −4.342 | −1.351 | 1.00 | 0.00 |
| ATOM | 158 | HD2 | ARG | 9 | −10.556 | −5.439 | −1.125 | 1.00 | 0.00 |
| ATOM | 159 | NE | ARG | 9 | −10.781 | −4.677 | −3.096 | 1.00 | 0.00 |
| ATOM | 160 | HE | ARG | 9 | −11.439 | −4.252 | −3.684 | 1.00 | 0.00 |
| ATOM | 161 | CZ | ARG | 9 | −9.794 | −5.361 | −3.607 | 1.00 | 0.00 |
| ATOM | 162 | NH1 | ARG | 9 | −8.770 | −5.684 | −2.865 | 1.00 | 0.00 |
| ATOM | 163 | HH11 | ARG | 9 | −8.742 | −5.408 | −1.904 | 1.00 | 0.00 |
| ATOM | 164 | HH12 | ARG | 9 | −8.014 | −6.208 | −3.256 | 1.00 | 0.00 |
| ATOM | 165 | NH2 | ARG | 9 | −9.831 | −5.723 | −4.860 | 1.00 | 0.00 |
| ATOM | 166 | HH21 | ARG | 9 | −10.615 | −5.476 | −5.429 | 1.00 | 0.00 |
| ATOM | 167 | HH22 | ARG | 9 | −9.074 | −6.247 | −5.252 | 1.00 | 0.00 |
| ATOM | 168 | C | ARG | 9 | −12.504 | −2.167 | −0.705 | 1.00 | 0.00 |
| ATOM | 169 | OT1 | ARG | 9 | −13.492 | −2.425 | −1.372 | 1.00 | 0.00 |
| ATOM | 170 | OT2 | ARG | 9 | −12.324 | −2.570 | 0.433 | 1.00 | 0.00 |
| END | | | | | | | | | |

REMARK FILENAME="refine_1_20.pdb"
REMARK ================================================================
REMARK overall,bonds,angles,improper,vdw,noe,cdih
REMARK energies: 104.733, 3.47295, 70.7767, 3.51384, 6.64866, 20.3204,
$CDIH
REMARK ================================================================
REMARK bonds,angles,impropers,noe,cdih
REMARK rms-d: 4.442149E−03,1.21652,0.496579,7.90724E−02,0
REMARK ================================================================
REMARK noe, cdih
REMARK violations.: 0, 0
REMARK ================================================================
REMARK DATE: 03-Apr-00 08:41:00       created by user: orish

| | | | | | | | | | |
|---|---|---|---|---|---|---|---|---|---|
| ATOM | 1 | CA | ILE | 1B | −9.783 | −1.457 | −0.558 | 1.00 | 0.00 |
| ATOM | 2 | HA | ILE | 1B | −9.677 | −0.665 | −1.298 | 1.00 | 0.00 |
| ATOM | 3 | CB | ILE | 1B | −11.259 | −1.637 | −0.199 | 1.00 | 0.00 |
| ATOM | 4 | HB | ILE | 1B | −11.578 | −0.796 | 0.417 | 1.00 | 0.00 |
| ATOM | 5 | CG1 | ILE | 1B | −11.441 | −2.945 | 0.598 | 1.00 | 0.00 |
| ATOM | 6 | HG11 | ILE | 1B | −12.251 | −2.816 | 1.316 | 1.00 | 0.00 |
| ATOM | 7 | HG12 | ILE | 1B | −10.519 | −3.167 | 1.135 | 1.00 | 0.00 |
| ATOM | 8 | CG2 | ILE | 1B | −12.101 | −1.660 | −1.481 | 1.00 | 0.00 |
| ATOM | 9 | HG21 | ILE | 1B | −12.492 | −0.662 | −1.677 | 1.00 | 0.00 |
| ATOM | 10 | HG22 | ILE | 1B | −12.930 | −2.357 | −1.358 | 1.00 | 0.00 |
| ATOM | 11 | HG23 | ILE | 1B | −11.480 | −1.978 | −2.318 | 1.00 | 0.00 |
| ATOM | 12 | CD1 | ILE | 1B | −11.776 | −4.119 | −0.334 | 1.00 | 0.00 |
| ATOM | 13 | HD11 | ILE | 1B | −11.998 | −5.004 | 0.263 | 1.00 | 0.00 |
| ATOM | 14 | HD12 | ILE | 1B | −10.926 | −4.325 | −0.983 | 1.00 | 0.00 |
| ATOM | 15 | HD13 | ILE | 1B | −12.644 | −3.866 | −0.941 | 1.00 | 0.00 |
| ATOM | 16 | C | ILE | 1B | −8.973 | −1.137 | 0.677 | 1.00 | 0.00 |
| ATOM | 17 | O | ILE | 1B | −9.510 | −0.787 | 1.709 | 1.00 | 0.00 |
| ATOM | 18 | N | ILE | 1B | −9.351 | −2.764 | −1.130 | 1.00 | 0.00 |
| ATOM | 19 | HT1 | ILE | 1B | −8.379 | −2.681 | −1.489 | 1.00 | 0.00 |
| ATOM | 20 | HT2 | ILE | 1B | −9.987 | −3.028 | −1.910 | 1.00 | 0.00 |
| ATOM | 21 | HT3 | ILE | 1B | −9.383 | −3.494 | −0.391 | 1.00 | 0.00 |
| ATOM | 22 | N | LEU | 2 | −7.676 | −1.250 | 0.593 | 1.00 | 0.00 |
| ATOM | 23 | HN | LEU | 2 | −7.221 | −1.531 | −0.230 | 1.00 | 0.00 |
| ATOM | 24 | CA | LEU | 2 | −6.745 | −0.970 | 1.725 | 1.00 | 0.00 |
| ATOM | 25 | HA | LEU | 2 | −7.286 | −0.659 | 2.617 | 1.00 | 0.00 |
| ATOM | 26 | CB | LEU | 2 | −6.051 | −2.305 | 1.992 | 1.00 | 0.00 |
| ATOM | 27 | HB1 | LEU | 2 | −5.606 | −2.675 | 1.069 | 1.00 | 0.00 |
| ATOM | 28 | HB2 | LEU | 2 | −6.782 | −3.027 | 2.359 | 1.00 | 0.00 |
| ATOM | 29 | CG | LEU | 2 | −4.955 | −2.110 | 3.041 | 1.00 | 0.00 |
| ATOM | 30 | HG | LEU | 2 | −5.142 | −1.190 | 3.595 | 1.00 | 0.00 |
| ATOM | 31 | CD1 | LEU | 2 | −4.955 | −3.296 | 4.007 | 1.00 | 0.00 |
| ATOM | 32 | HD11 | LEU | 2 | −5.261 | −2.958 | 4.997 | 1.00 | 0.00 |
| ATOM | 33 | HD12 | LEU | 2 | −3.952 | −3.720 | 4.062 | 1.00 | 0.00 |
| ATOM | 34 | HD13 | LEU | 2 | −5.651 | −4.055 | 3.651 | 1.00 | 0.00 |
| ATOM | 35 | CD2 | LEU | 2 | −3.595 | −2.020 | 2.345 | 1.00 | 0.00 |
| ATOM | 36 | HD21 | LEU | 2 | −3.732 | −1.671 | 1.322 | 1.00 | 0.00 |
| ATOM | 37 | HD22 | LEU | 2 | −3.127 | −3.004 | 2.334 | 1.00 | 0.00 |
| ATOM | 38 | HD23 | LEU | 2 | −2.956 | −1.320 | 2.884 | 1.00 | 0.00 |
| ATOM | 39 | C | LEU | 2 | −5.725 | 0.080 | 1.347 | 1.00 | 0.00 |
| ATOM | 40 | O | LEU | 2 | −4.915 | 0.491 | 2.155 | 1.00 | 0.00 |

TABLE 3-continued

| | | | | | | | | | |
|---|---|---|---|---|---|---|---|---|---|
| ATOM | 41 | N | SER | 3 | −5.747 | 0.528 | 0.122 | 1.00 | 0.00 |
| ATOM | 42 | HN | SER | 3 | −6.390 | 0.212 | −0.547 | 1.00 | 0.00 |
| ATOM | 43 | CA | SER | 3 | −4.806 | 1.562 | −0.398 | 1.00 | 0.00 |
| ATOM | 44 | HA | SER | 3 | −4.771 | 1.557 | −1.486 | 1.00 | 0.00 |
| ATOM | 45 | CB | SER | 3 | −5.388 | 2.889 | 0.083 | 1.00 | 0.00 |
| ATOM | 46 | HB1 | SER | 3 | −6.272 | 3.133 | −0.510 | 1.00 | 0.00 |
| ATOM | 47 | HB2 | SER | 3 | −4.648 | 3.677 | −0.034 | 1.00 | 0.00 |
| ATOM | 48 | OG | SER | 3 | −5.738 | 2.778 | 1.457 | 1.00 | 0.00 |
| ATOM | 49 | HG | SER | 3 | −6.250 | 3.554 | 1.696 | 1.00 | 0.00 |
| ATOM | 50 | C | SER | 3 | −3.416 | 1.369 | 0.164 | 1.00 | 0.00 |
| ATOM | 51 | O | SER | 3 | −3.131 | 1.747 | 1.283 | 1.00 | 0.00 |
| ATOM | 52 | N | ARG | 4 | −2.534 | 0.782 | −0.597 | 1.00 | 0.00 |
| ATOM | 53 | HN | ARG | 4 | −2.747 | 0.466 | −1.515 | 1.00 | 0.00 |
| ATOM | 54 | CA | ARG | 4 | −1.116 | 0.522 | −0.175 | 1.00 | 0.00 |
| ATOM | 55 | HA | ARG | 4 | −0.840 | 1.104 | 0.716 | 1.00 | 0.00 |
| ATOM | 56 | CB | ARG | 4 | −1.095 | −0.975 | 0.176 | 1.00 | 0.00 |
| ATOM | 57 | HB1 | ARG | 4 | −1.739 | −1.526 | −0.506 | 1.00 | 0.00 |
| ATOM | 58 | HB2 | ARG | 4 | −1.453 | −1.114 | 1.200 | 1.00 | 0.00 |
| ATOM | 59 | CG | ARG | 4 | 0.323 | −1.521 | 0.077 | 1.00 | 0.00 |
| ATOM | 60 | HG1 | ARG | 4 | 1.018 | −0.714 | −0.142 | 1.00 | 0.00 |
| ATOM | 61 | HG2 | ARG | 4 | 0.369 | −2.273 | −0.711 | 1.00 | 0.00 |
| ATOM | 62 | CD | ARG | 4 | 0.681 | −2.146 | 1.415 | 1.00 | 0.00 |
| ATOM | 63 | HD1 | ARG | 4 | −0.203 | −2.604 | 1.849 | 1.00 | 0.00 |
| ATOM | 64 | HD2 | ARG | 4 | 1.067 | −1.373 | 2.079 | 1.00 | 0.00 |
| ATOM | 65 | NE | ARG | 4 | 1.715 | −3.169 | 1.096 | 1.00 | 0.00 |
| ATOM | 66 | HE | ARG | 4 | 2.519 | −3.100 | 1.652 | 1.00 | 0.00 |
| ATOM | 67 | CZ | ARG | 4 | 1.576 | −4.075 | 0.168 | 1.00 | 0.00 |
| ATOM | 68 | NH1 | ARG | 4 | 1.048 | −5.233 | 0.460 | 1.00 | 0.00 |
| ATOM | 69 | HH11 | ARG | 4 | 0.750 | −5.424 | 1.395 | 1.00 | 0.00 |
| ATOM | 70 | HH12 | ARG | 4 | 0.942 | −5.927 | −0.252 | 1.00 | 0.00 |
| ATOM | 71 | NH2 | ARG | 4 | 1.965 | −3.825 | −1.052 | 1.00 | 0.00 |
| ATOM | 72 | HH21 | ARG | 4 | 2.370 | −2.938 | −1.276 | 1.00 | 0.00 |
| ATOM | 73 | HH22 | ARG | 4 | 1.859 | −4.520 | −1.764 | 1.00 | 0.00 |
| ATOM | 74 | C | ARG | 4 | −0.156 | 0.835 | −1.306 | 1.00 | 0.00 |
| ATOM | 75 | O | ARG | 4 | 0.292 | −0.044 | −2.015 | 1.00 | 0.00 |
| ATOM | 76 | N | ARG | 5 | 0.150 | 2.088 | −1.507 | 1.00 | 0.00 |
| ATOM | 77 | HN | ARG | 5 | −0.225 | 2.805 | −0.970 | 1.00 | 0.00 |
| ATOM | 78 | CA | ARG | 5 | 1.062 | 2.546 | −2.605 | 1.00 | 0.00 |
| ATOM | 79 | HA | ARG | 5 | 1.447 | 1.693 | −3.157 | 1.00 | 0.00 |
| ATOM | 80 | CB | ARG | 5 | 0.167 | 3.349 | −3.540 | 1.00 | 0.00 |
| ATOM | 81 | HB1 | ARG | 5 | 0.684 | 3.496 | −4.489 | 1.00 | 0.00 |
| ATOM | 82 | HB2 | ARG | 5 | −0.044 | 4.319 | −3.089 | 1.00 | 0.00 |
| ATOM | 83 | CG | ARG | 5 | −1.142 | 2.596 | −3.784 | 1.00 | 0.00 |
| ATOM | 84 | HG1 | ARG | 5 | −1.832 | 3.235 | −4.334 | 1.00 | 0.00 |
| ATOM | 85 | HG2 | ARG | 5 | −1.587 | 2.319 | −2.828 | 1.00 | 0.00 |
| ATOM | 86 | CD | ARG | 5 | −0.861 | 1.333 | −4.602 | 1.00 | 0.00 |
| ATOM | 87 | HD1 | ARG | 5 | −1.790 | 0.801 | −4.798 | 1.00 | 0.00 |
| ATOM | 88 | HD2 | ARG | 5 | −0.168 | 0.687 | −4.058 | 1.00 | 0.00 |
| ATOM | 89 | NE | ARG | 5 | −0.259 | 1.834 | −5.868 | 1.00 | 0.00 |
| ATOM | 90 | HE | ARG | 5 | 0.592 | 1.404 | −6.094 | 1.00 | 0.00 |
| ATOM | 91 | CZ | ARG | 5 | −0.804 | 2.756 | −6.613 | 1.00 | 0.00 |
| ATOM | 92 | NH1 | ARG | 5 | −2.099 | 2.919 | −6.607 | 1.00 | 0.00 |
| ATOM | 93 | HH11 | ARG | 5 | −2.673 | 2.338 | −6.031 | 1.00 | 0.00 |
| ATOM | 94 | HH12 | ARG | 5 | −2.516 | 3.626 | −7.178 | 1.00 | 0.00 |
| ATOM | 95 | NH2 | ARG | 5 | −0.054 | 3.515 | −7.365 | 1.00 | 0.00 |
| ATOM | 96 | HH21 | ARG | 5 | 0.938 | 3.389 | −7.370 | 1.00 | 0.00 |
| ATOM | 97 | HH22 | ARG | 5 | −0.472 | 4.221 | −7.936 | 1.00 | 0.00 |
| ATOM | 98 | C | ARG | 5 | 2.235 | 3.432 | −2.176 | 1.00 | 0.00 |
| ATOM | 99 | O | ARG | 5 | 3.149 | 3.598 | −2.959 | 1.00 | 0.00 |
| ATOM | 100 | N | PRO | 6 | 2.225 | 4.009 | −0.990 | 1.00 | 0.00 |
| ATOM | 101 | CA | PRO | 6 | 3.362 | 4.885 | −0.604 | 1.00 | 0.00 |
| ATOM | 102 | HA | PRO | 6 | 3.562 | 5.623 | −1.380 | 1.00 | 0.00 |
| ATOM | 103 | CB | PRO | 6 | 2.877 | 5.579 | 0.665 | 1.00 | 0.00 |
| ATOM | 104 | HB1 | PRO | 6 | 2.405 | 6.534 | 0.423 | 1.00 | 0.00 |
| ATOM | 105 | HB2 | PRO | 6 | 3.704 | 5.730 | 1.362 | 1.00 | 0.00 |
| ATOM | 106 | CG | PRO | 6 | 1.867 | 4.642 | 1.236 | 1.00 | 0.00 |
| ATOM | 107 | HG1 | PRO | 6 | 1.119 | 5.192 | 1.780 | 1.00 | 0.00 |
| ATOM | 108 | HG2 | PRO | 6 | 2.357 | 3.932 | 1.887 | 1.00 | 0.00 |
| ATOM | 109 | CD | PRO | 6 | 1.228 | 3.922 | 0.080 | 1.00 | 0.00 |
| ATOM | 110 | HD2 | PRO | 6 | 1.038 | 2.890 | 0.343 | 1.00 | 0.00 |
| ATOM | 111 | HD1 | PRO | 6 | 0.316 | 4.415 | −0.219 | 1.00 | 0.00 |
| ATOM | 112 | C | PRO | 6 | 4.587 | 4.040 | −0.334 | 1.00 | 0.00 |
| ATOM | 113 | O | PRO | 6 | 5.195 | 4.120 | 0.714 | 1.00 | 0.00 |
| ATOM | 114 | N | SRP | 7 | 4.973 | 3.235 | −1.287 | 1.00 | 0.00 |
| ATOM | 115 | HN | SRP | 7 | 4.501 | 3.180 | −2.153 | 1.00 | 0.00 |
| ATOM | 116 | CA | SRP | 7 | 6.178 | 2.345 | −1.198 | 1.00 | 0.00 |
| ATOM | 117 | C | SRP | 7 | 5.986 | 1.217 | −0.187 | 1.00 | 0.00 |
| ATOM | 118 | O | SRP | 7 | 6.890 | 0.401 | 0.000 | 1.00 | 0.00 |
| ATOM | 119 | CB | SRP | 7 | 7.409 | 3.196 | −0.806 | 1.00 | 0.00 |

TABLE 3-continued

| | | | | | | | | |
|---|---|---|---|---|---|---|---|---|
| ATOM | 120 | OG1 | SRP | 7 | 7.614 | 4.247 | −1.816 | 1.00 | 0.00 |
| ATOM | 121 | PG2 | SRP | 7 | 9.111 | 4.826 | −1.692 | 1.00 | 0.00 |
| ATOM | 122 | OG3 | SRP | 7 | 9.841 | 4.741 | −3.126 | 1.00 | 0.00 |
| ATOM | 123 | OG2 | SRP | 7 | 9.883 | 4.016 | −0.692 | 1.00 | 0.00 |
| ATOM | 124 | OG4 | SRP | 7 | 9.056 | 6.362 | −1.210 | 1.00 | 0.00 |
| ATOM | 125 | HA | SRP | 7 | 6.354 | 1.890 | −2.170 | 1.00 | 0.00 |
| ATOM | 126 | HG3 | SRP | 7 | 10.770 | 4.312 | −3.012 | 1.00 | 0.00 |
| ATOM | 127 | HG4 | SRP | 7 | 8.124 | 6.751 | −1.413 | 1.00 | 0.00 |
| ATOM | 128 | HB1 | SRP | 7 | 8.290 | 2.553 | −0.751 | 1.00 | 0.00 |
| ATOM | 129 | HB2 | SRP | 7 | 7.240 | 3.659 | 0.163 | 1.00 | 0.00 |
| ATOM | 130 | N | TYR | 8 | 4.845 | 1.147 | 0.452 | 1.00 | 0.00 |
| ATOM | 131 | HN | TYR | 8 | 4.121 | 1.772 | 0.312 | 1.00 | 0.00 |
| ATOM | 132 | CA | TYR | 8 | 4.521 | 0.098 | 1.463 | 1.00 | 0.00 |
| ATOM | 133 | HA | TYR | 8 | 4.788 | 0.421 | 2.466 | 1.00 | 0.00 |
| ATOM | 134 | CB | TYR | 8 | 3.001 | −0.061 | 1.371 | 1.00 | 0.00 |
| ATOM | 135 | HB1 | TYR | 8 | 2.757 | −1.115 | 1.255 | 1.00 | 0.00 |
| ATOM | 136 | HB2 | TYR | 8 | 2.631 | 0.495 | 0.510 | 1.00 | 0.00 |
| ATOM | 137 | CG | TYR | 8 | 2.351 | 0.471 | 2.630 | 1.00 | 0.00 |
| ATOM | 138 | CD1 | TYR | 8 | 2.895 | 0.164 | 3.884 | 1.00 | 0.00 |
| ATOM | 139 | HD1 | TYR | 8 | 3.776 | −0.453 | 3.953 | 1.00 | 0.00 |
| ATOM | 140 | CD2 | TYR | 8 | 1.202 | 1.269 | 2.544 | 1.00 | 0.00 |
| ATOM | 141 | HD2 | TYR | 8 | 0.776 | 1.504 | 1.579 | 1.00 | 0.00 |
| ATOM | 142 | CE1 | TYR | 8 | 2.293 | 0.655 | 5.048 | 1.00 | 0.00 |
| ATOM | 143 | HE1 | TYR | 8 | 2.713 | 0.417 | 6.014 | 1.00 | 0.00 |
| ATOM | 144 | CE2 | TYR | 8 | 0.600 | 1.759 | 3.710 | 1.00 | 0.00 |
| ATOM | 145 | HE2 | TYR | 8 | −0.284 | 2.374 | 3.643 | 1.00 | 0.00 |
| ATOM | 146 | CZ | TYR | 8 | 1.146 | 1.452 | 4.961 | 1.00 | 0.00 |
| ATOM | 147 | OH | TYR | 8 | 0.553 | 1.936 | 6.110 | 1.00 | 0.00 |
| ATOM | 148 | HH | TYR | 8 | 1.222 | 2.407 | 6.613 | 1.00 | 0.00 |
| ATOM | 149 | C | TYR | 8 | 5.198 | −1.217 | 1.126 | 1.00 | 0.00 |
| ATOM | 150 | O | TYR | 8 | 5.057 | −1.728 | 0.033 | 1.00 | 0.00 |
| ATOM | 151 | N | ARG | 9 | 5.936 | −1.788 | 2.046 | 1.00 | 0.00 |
| ATOM | 152 | HN | ARG | 9 | 6.065 | −1.397 | 2.951 | 1.00 | 0.00 |
| ATOM | 153 | CA | ARG | 9 | 6.655 | −3.095 | 1.832 | 1.00 | 0.00 |
| ATOM | 154 | HA | ARG | 9 | 5.958 | −3.901 | 1.569 | 1.00 | 0.00 |
| ATOM | 155 | CB | ARG | 9 | 7.597 | −2.847 | 0.639 | 1.00 | 0.00 |
| ATOM | 156 | HB1 | ARG | 9 | 7.078 | −2.256 | −0.115 | 1.00 | 0.00 |
| ATOM | 157 | HB2 | ARG | 9 | 7.886 | −3.805 | 0.204 | 1.00 | 0.00 |
| ATOM | 158 | CG | ARG | 9 | 8.858 | −2.097 | 1.089 | 1.00 | 0.00 |
| ATOM | 159 | HG1 | ARG | 9 | 8.772 | −1.825 | 2.139 | 1.00 | 0.00 |
| ATOM | 160 | HG2 | ARG | 9 | 8.975 | −1.193 | 0.489 | 1.00 | 0.00 |
| ATOM | 161 | CD | ARG | 9 | 10.085 | −2.996 | 0.895 | 1.00 | 0.00 |
| ATOM | 162 | HD1 | ARG | 9 | 10.070 | −3.810 | 1.617 | 1.00 | 0.00 |
| ATOM | 163 | HD2 | ARG | 9 | 10.998 | −2.408 | 1.013 | 1.00 | 0.00 |
| ATOM | 164 | NE | ARG | 9 | 9.950 | −3.518 | −0.493 | 1.00 | 0.00 |
| ATOM | 165 | HE | ARG | 9 | 9.658 | −4.453 | −0.534 | 1.00 | 0.00 |
| ATOM | 166 | CZ | ARG | 9 | 10.193 | −2.808 | −1.561 | 1.00 | 0.00 |
| ATOM | 167 | NH1 | ARG | 9 | 11.414 | −2.436 | −1.833 | 1.00 | 0.00 |
| ATOM | 168 | HH11 | ARG | 9 | 12.163 | −2.695 | −1.223 | 1.00 | 0.00 |
| ATOM | 169 | HH12 | ARG | 9 | 11.600 | −1.892 | −2.651 | 1.00 | 0.00 |
| ATOM | 170 | NH2 | ARG | 9 | 9.215 | −2.471 | −2.357 | 1.00 | 0.00 |
| ATOM | 171 | HH21 | ARG | 9 | 8.280 | −2.756 | −2.149 | 1.00 | 0.00 |
| ATOM | 172 | HH22 | ARG | 9 | 9.402 | −1.927 | −3.175 | 1.00 | 0.00 |
| ATOM | 173 | C | ARG | 9 | 7.449 | −3.492 | 3.057 | 1.00 | 0.00 |
| ATOM | 174 | OT1 | ARG | 9 | 7.344 | −2.801 | 4.057 | 1.00 | 0.00 |
| ATOM | 175 | OT2 | ARG | 9 | 8.155 | −4.485 | 2.985 | 1.00 | 0.00 |
| END | | | | | | | | | |

REFERENCES

American Diabetes Association, "Standards of Medical Care for Patients With Diabetes Mellitus", 21 Diabetes Care (1998)

Barber A J, Nakamura M, Wolpert E B, et al Insulin Rescues Retinal Neurons from Apoptosis by a Phosphatidylinositol 3-Kinase/Akt-mediated Mechanism That Reduces the Activation of Caspase-3. J Biol Chem 276:32814–821 (2001).

Bijur G N, De Sarno P, R S. J Glycogen synthase kinase-3beta facilitates staurosporine- and heat shock-induced apoptosis. Protection by lithium J Biol Chem 275:7583–90 (2000).

Burke et al, "Nonhydrolyzable phosphotyrosyl mimetics for the preparation of phosphatase-resistant SH2 domain inhibitors", Biochemistry 33(21):6490–6494 (1994a)

Burke et al, "Potent inhibition of insulin receptor dephosphorylation by a hexamer peptide containing the phosphotyrosyl mimetic F2Pmp", Biochem Biophys Res Commun 204(1):129–133 (1994b)

Burke et al, "4'-O-[2-(2-fluoromalonyl)]-L-tyrosine: a phosphotyrosyl mimic for the preparation of signal transduction inhibitory peptides", J Med Chem 39(5):1021–1027 (1996a)

Burke et al, "Small molecule interactions with protein-tyrosine phosphatase PTP1B and their use in inhibitor design", Biochemistry 35(50):15989–15996 (1996b)

Chen et al, "Why is phosphonodifluoromethyl phenylalanine a more potent inhibitory moiety than phosphonomethyl phenylalanine toward protein-tyrosine phosphatases?", *Biochem Biophys Res Commun* 216(3):976–984 (1995)

Cheng K, Creacy S, Larner J Insulin-like effect of lithium ion on isolated rat adipocytes stimulation of glycogenesis beyond glucose transport. *Mol. Cell. Biochem.* 56:177–182 (1983).

Chu et al, "Sequential phosphorylation by mitogen-activated protein kinase and glycogen synthase kinase 3 represses transcriptional activation by heat shock factor-1", *J Biol Chem* 271(48):30847–30857 (1996)

Cross et al, "Inhibition of glycogen synthase kinase-3 by insulin mediated by protein kinase B", *Nature* 378(6559): 785–78 (1995)

Cross D A, Culbert A A, Chalmers K A, Facci L, Skaper S D, A D. R Selective small-molecule inhibitors of glycogen synthase kinase-3 activity protect primary neurones from death. *J Neurochem* 77:94–102 (2001).

Crowder R J, R S. F Glycogen synthase kinase-3 beta activity is critical for neuronal death caused by inhibiting phosphatidylinositol 3-kinase or Akt but not for death caused by nerve growth factor withdrawal. *J Biol Chem* 275:34266–71 (2000).

Dajani et al., "Crystal structure of glycogen synthase kinase 3β: structural basis for phosphate-primed substrate specificity and auto inhibition", *Cell* 105:721–732 (2001)

Devlin, *Textbook of Biochemistry with Clinical Correlations*, 4th Ed. (Wiley-Liss, Inc., 1997)

Dugas et al, *Bioorganic Chemistry* (Springer-Verlag, New York, 1981), pp 54–92

Eldar-Finkelman et al, "Expression and characterization of glycogen synthase kinase-3 mutants and their effect on glycogen synthase activity in intact cells", *Proc Natl Acad Sci USA* 93(19):10228–10233 (1996)

Eldar-Finkelman et al, "Phosphorylation of insulin receptor substrate 1 by glycogen synthase kinase 3 impairs insulin action", *Proc Natl Acad Sci USA* 94(18):9660–9664 (1997)

Eldar-Finkelman et al, "Increased glycogen synthase kinase-3 activity in diabetes- and obesity-prone C57BL/6J mice", *Diabetes* 48(8):1662–1666 (1999)

Fiol et al, "Formation of protein kinase recognition sites by covalent modification of the substrate. Molecular mechanism for the synergistic action of casein kinase II and glycogen synthase kinase 3", *J Biol Chem* 262(29): 14042–14048 (1987)

Fiol et al, "Phosphoserine as a recognition determinant for glycogen synthase kinase-3: phosphorylation of a synthetic peptide based on the G-component of protein phosphatase-1 *Arch Biochem Biophys* 267(2):797–802 (1988)

Fiol et al, "Ordered multisite protein phosphorylation. Analysis of glycogen synthase kinase 3 action using model peptide substrates", *J Biol Chem* 265(11):6061–6065 (1990)

Fiol et al, "A secondary phosphorylation of CREB341 at Ser129 is required for the cAMP-mediated control of gene expression. A role for glycogen synthase kinase-3 in the control of gene expression", *J Biol Chem* 269(51):32187–32193 (1994)

Fu et al, Design and synthesis of a pyridone-based phosphotyrosine mimetic", *Bioorg Med Chem Lett* 8(19): 2813–2816 (1998)

Gao et al, "Inhibition of Grb2 SH2 domain binding by non-phosphate-containing ligands. 2. 4-(2-Malonyl)phenylalanine as a potent phosphotyrosyl mimetic", *J Med Chem* 43(5):911–920 (2000)

Gething et al, "Cell-surface expression of influenza haemagglutinin from a cloned DNA copy of the RNA gene *Nature* 293(5834):620–625 (1981)

Groves et al, "Structural basis for inhibition of the protein tyrosine phosphatase 1B by phosphotyrosine peptide mimetics", *Biochemistry* 37(51):17773–17783 (1998)

Hallstrom et al, "Regulation of transcription factor Pdr1p function by an Hsp70 protein in *Saccharomyces cerevisiae*", *Mol Cell Biol* 18(3):1147–1155 (1998)

Hanger D P, Hughes K, Woodgett J R, Brion J P, Anderton B H Glycogen synthase kinase-3 induces Alzheimer's disease-like phosphorylation of tau: generation of paired helical filament epitopes and neuronal localisation of the kinase. *Neurosci. Lett.* 147:58–62 (1992).

Hawiger J, "Cellular import of functional peptides to block intracellular signaling *Curr Opin Immunol* 9(2):189–194 (1997)

He et al, Glycogen synthase kinase-3 and dorsoventral patterning in Xenopus embryos", *Nature* 374(6523):617–622 (1995)

Higashimoto et al, "Human p53 is phosphorylated on serines 6 and 9 in response to DNA damage-inducing agents", *J Biol Chem* 275(30):23199–23203 (2000)

Klein P S, Melton D A "A Molecular Mechanism for the Effect of Lithium on Development". *Proc. Natl. Acad. Sci. USA* 93:8455–8459 (1996).

Kole et al, "Protein-tyrosine phosphatase inhibition by a peptide containing the phosphotyrosyl mimetic, L-O-malonyltyrosine", *Biochem Biophys Res Commun* 209(3): 817–822 (1995)2

Kole et al, "Specific inhibition of insulin receptor dephosphorylation by a synthetic dodecapeptide containing sulfotyrosyl residues as phosphotyrosyl mimetic", *Indian J Biochem Biophys* 34(1–2):50–55 (1997)

Latimer et al, "Stimulation of MAP kinase by v-raf transformation of fibroblasts fails to induce hyperphosphorylation of transfected tau", *FEBS Lett* 365:42–46 (1995)

Lucas J J, Hernandez F, Gomez-Ramos P, Moran M A, Hen R, J. A "Decreased nuclear beta-catenin, tahyperphosphorylation and neurodegeneration in GSK-3beta conditional transgenic mice". *EMBO J* 20:27–39 (2001).

Lovestone et al, *Curr Biol* 4:1077–1086 (1995)

Mandelkow et al, "Tau as a marker for Alzheimer's disease", *Trends Biochem Sci.* 18(12):480–483 (1983)

Mandelkow E M, Drewes G, Biernat J, et al "Glycogen synthase kinase-3 and the Alzheimer-like state of microtubule-associated protein tau". *Febs Lett.* 314:315–21 (1992).

Manji et al, "Lithium at 50: have the neuroprotective effects of this unique cation been overlooked?", *Biol Psychiatry* 46(7):929–940 (1999)

McKinsey et al, "Phosphorylation of the PEST domain of IkappaBbeta regulates the function of NF-kappaB/IkappaBbeta complexes", *J Biol Chem* 272(36):22377–22380 (1997)

Merrifield et al, *J Am Chem Soc* 85:2149 (1964)

Mikol et al, "The crystal structures of the SH2 domain of p56lck complexed with two phosphonopeptides suggest a gated peptide binding site", *J Mol Biol* 246(2):344–355 (1995)

Morrison et al, *Organic Chemistry*, 6th Ed. (Prentice Hall, 1992)

Mulot et al, "PHF-tau from Alzheimer's brain comprises four species on SDS-PAGE which can be mimicked by in vitro phosphorylation of human brain tau by glycogen synthase kinase-3 beta", *FEBS Lett* 349(3):359–364 (1994)

Mulot et al, "Phosphorylation of tau by glycogen synthase kinase-3 beta in vitro produces species with similar electrophoretic and immunogenic properties to PHF-tau from Alzheimer's disease brain", *Biochem Soc Trans* 23(1):45S (1995)

Myers et al, "RS-1 activates phosphatidylinositol 3'-kinase by associating with src homology 2 domains of p85d", *Proc Natl Acad Sci USA* 89(21):10350–10354 (1992)

Nicolaou et al, "Design and synthesis of a peptidomimeticemploying β-D-glucose for scaffolding" in *Peptides*, Rivier and Marshall (eds) ESCOM (1990)

Nikoulina et al, "Regulation of glycogen synthase activity in cultured skeletal muscle cells from subjects with type II diabetes: role of chronic hyperinsulinemia and hyperglycemia", *Diabetes* 46(6):1017–1024 (1997)

Nikoulina et al, "Potential role of glycogen synthase kinase-3 in skeletal muscle insulin resistance of type 2 diabetes", *Diabetes* 49(2):263–271 (2000)

Nonaka et al., *Proc. Natl. Acad. Sci. USA*, 95:2642–2647 (1998)

Otaka et al, *Tetrahedron Lett* 36(6):927–30 (1995)

Otaka et al, *Chem Commun* (12):1081–1082 (2000)

Pap M, Cooper G "Role of glycogen synthase kinase-3 in the phosphatidylinositol 3-Kinase/Akt cell survival pathway". *J. Biol. Chem.* 273:19929–32 (1998).

Phiel C J, P S. K "Molecular targets of lithium action". *Annu Rev Pharmacol Toxicol* 41:789–813 (2001).

Rich D H, in Protease Inhibitors, Barrett and Selveson (eds) Elsevier (1986)

Roller et al, "Potent inhibition of protein-tyrosine phosphatase-1B using the phosphotyrosyl mimetic fluoro-O-malonyl tyrosine (FOMT)", *Bioorg Med Chem Lett* 8(16):2149–2150 (1998)

Rubinfeld et al, "Binding of GSK3beta to the APC-beta-catenin complex and regulation of complex assembly", *Science* 272(5264):1023–1026 (1996)

Sambrook et al, *Molecular Cloning: A Laboratory Manual*, 2nd Ed. (Cold Spring Harbor Press, 1989)

Schiller et al, *Int J Pent Prot Res* 25:171 (1985)

Shapiro et al, "Combined Fmoc-Alloc strategy for a general SPPS of phosphoserine peptides; preparation of phosphorylation-dependent tau antisera", *Bioorg Med Chem* 5(1): 147–56 (1997)

Sherman et al, *J Am Chem Soc* 112:433 (1990)

Shulman et al, "Quantitation of muscle glycogen synthesis in normal subjects and subjects with non-insulin-dependent diabetes by 13C nuclear magnetic resonance spectroscopy", *N Engl J Med* 322(4):223–228 (1990)

Stambolic V, Ruel L, Woodgett J R "Lithium inhibits glycogen synthase kinase-3 activity and mimics wingless signalling in intact cells". *Curr. Biol.* 6:1664–1668 (1996).

ter Haar et al., "Structure of GSK-3 beta reveals a primed phosphorylation mechanism", *Nat. Struct. Biol.* 8(7):593–6 (2001)

Thomas, *J. Am. Geriatr. Soc.*, 43:1279–89 (1995)

Thorsett et al, "Dipeptide mimics. Conformationally restricted inhibitors of angiotensin-converting enzyme", *Biochem Biophys Res Commun* 111(1):166–171 (1983)

Tong N, Sanchez J F, Maggirwar S B, et al "Activation of glycogen synthase kinase 3 beta (GSK-3beta) by platelet activating factor mediates migration and cell death in cerebellar granule neurons". *Eur J Neurosci* 13:1913–22 (2001).

Veber et al, "Conformationally restricted bicyclic analogs of somatostatin", *Proc Natl Acad Sci USA* 75(6):2636–2640 (1978)

Welsh et al, "Glycogen synthase kinase-3 is rapidly inactivated in response to insulin and phosphorylates eukaryotic initiation factor eIF-2B", *Biochem J* 294(Pt 3):625–629 (1993)

Wiemann et al, Tetrahedron 56:1331–1337 (2000)

Ye et al, "L-O-(2-malonyl)tyrosine: a new phosphotyrosyl mimetic for the preparation of Src homology 2 domain inhibitory peptides", *J Med Chem* 38(21):4270–4275 (1995)

---

What is claimed is:

1. A peptide inhibitor of glycogen synthase kinase-3 (GSK-3), comprising a polypeptide having between 7 and 20 amino acid residues and the amino acid sequence XZXXXS(p)X, wherein:
   S(p)=phosphorylated serine or threonine,
   X=any amino acid, whereas at least one of X is a proline residue, and
   Z=any amino acid except serine or threonine,
   said amino acid sequence being a part of the GSK-3 substrate heat shock factor-1(HSF-1) protein containing a single SXXXS(p) recognition motif, wherein S is serine and S(p) is a phosphorylated serine, in which S is replaced by said Z,
   with the proviso that the polypeptide does not contain two or more SXXXS motifs, wherein S=serine, upstream of the S(p) residue,
   said polypeptide being capable of inhibiting the enzymatic activity of GSK-3.

2. A peptide inhibitor in accordance with claim 1, wherein said polypeptide has a length of from 10 to 13 amino acids.

3. A peptide inhibitor in accordance with claim 1, wherein said polypeptide has a length of at least 8 amino acid residues.

4. A peptide inhibitor in accordance with claim 1, having at least three amino acid residues upstream of the Z amino acid residue.

5. A peptide inhibitor in accordance with claim 4, wherein an amino acid residue at the position three residues upstream of Z is an amino acid residue other than a glutamic acid residue.

6. A pharmaceutical composition, identified for use in the treatment of a biological condition mediated by GSK-3, comprising the peptide inhibitor of claim 1 in a pharmaceutically acceptable excipient.

* * * * *